US012357593B2

(12) United States Patent
Tuohy et al.

(10) Patent No.: US 12,357,593 B2
(45) Date of Patent: *Jul. 15, 2025

(54) OVARIAN CANCER VACCINES

(71) Applicant: The Cleveland Clinic Foundation, Cleveland, OH (US)

(72) Inventors: Vincent K. Tuohy, Broadview Heights, OH (US); Suparna Mazumder, Olmsted Falls, OH (US); Justin M. Johnson, Willoughby Hills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/462,648

(22) Filed: Sep. 7, 2023

(65) Prior Publication Data
US 2024/0041798 A1    Feb. 8, 2024

Related U.S. Application Data

(63) Continuation of application No. 17/404,025, filed on Aug. 17, 2021, now Pat. No. 11,786,489, which is a continuation of application No. 15/757,151, filed as application No. PCT/US2016/050159 on Sep. 2, 2016, now Pat. No. 11,090,284.

(60) Provisional application No. 62/213,286, filed on Sep. 2, 2015.

(51) Int. Cl.
| | | |
|---|---|---|
| *A61K 31/138* | (2006.01) |
| *A61K 31/337* | (2006.01) |
| *A61K 31/4196* | (2006.01) |
| *A61K 31/4745* | (2006.01) |
| *A61K 31/4985* | (2006.01) |
| *A61K 31/502* | (2006.01) |
| *A61K 31/555* | (2006.01) |
| *A61K 31/675* | (2006.01) |
| *A61K 31/704* | (2006.01) |
| *A61K 31/7048* | (2006.01) |
| *A61K 31/7064* | (2006.01) |
| *A61K 31/7068* | (2006.01) |
| *A61K 33/243* | (2019.01) |
| *A61K 39/00* | (2006.01) |
| *A61K 40/11* | (2025.01) |
| *A61K 40/13* | (2025.01) |
| *A61K 40/24* | (2025.01) |
| *A61K 40/42* | (2025.01) |
| *A61K 45/06* | (2006.01) |
| *A61P 35/00* | (2006.01) |
| *A61K 33/244* | (2019.01) |

(52) U.S. Cl.
CPC .......... *A61K 31/138* (2013.01); *A61K 31/337* (2013.01); *A61K 31/4196* (2013.01); *A61K 31/4745* (2013.01); *A61K 31/4985* (2013.01); *A61K 31/502* (2013.01); *A61K 31/555* (2013.01); *A61K 31/675* (2013.01); *A61K 31/704* (2013.01); *A61K 31/7048* (2013.01); *A61K 31/7064* (2013.01); *A61K 31/7068* (2013.01); *A61K 33/243* (2019.01); *A61K 39/001102* (2018.08); *A61K 40/11* (2025.01); *A61K 40/13* (2025.01); *A61K 40/24* (2025.01); *A61K 40/4202* (2025.01); *A61K 45/06* (2013.01); *A61P 35/00* (2018.01); *A61K 33/244* (2019.01); *A61K 2039/575* (2013.01); *A61K 2239/59* (2023.05)

(58) Field of Classification Search
CPC .................................................. A61K 31/138
USPC ...................................................... 424/185.1
See application file for complete search history.

(56) References Cited

U.S. PATENT DOCUMENTS

| | | | | |
|---|---|---|---|---|
| 11,090,284 B2 * | 8/2021 | Tuohy | .................. | A61K 33/243 |
| 11,786,489 B2 * | 10/2023 | Tuohy | ................ | A61K 31/7068 |
| | | | | 424/133.1 |
| 2015/0004156 A1 | 1/2015 | Gaucher et al. | | |

FOREIGN PATENT DOCUMENTS

| | | |
|---|---|---|
| JP | 2004-521609 | 7/2004 |
| JP | 2005-533488 | 11/2005 |
| JP | 2014-517685 | 7/2014 |
| JP | 2015-506341 | 3/2015 |
| JP | 2015-516374 | 6/2015 |
| WO | WO 2002/012341 | 2/2002 |
| WO | WO 2003/080835 | 10/2003 |
| WO | WO 2005/005615 | 1/2005 |
| WO | WO 2012/140627 | 10/2012 |
| WO | WO 2013/136182 | 9/2013 |
| WO | WO 2014/153636 | 10/2014 |
| WO | WO 2015/114142 | 8/2015 |

OTHER PUBLICATIONS

Gouédard et al (JBC, 2000, 275(36): 27973-27978).*
Chowdhury et al (Journal of Immunological Methods, 2001, 249: 147-154).*
Weide et al (Immunology Letters, 2008, 115: 33-42).*
Alipour et al., Specific immunotherapy in ovarian cancer: a systematic review. Immunotherapy. Oct. 2016; 8(10):1193-204.

(Continued)

*Primary Examiner* — Sean E Aeder
(74) *Attorney, Agent, or Firm* — Jason R. Bond; Casimir Jones, S.C.

(57) ABSTRACT

Provided herein are methods, kits and compositions for the treatment and/or prevention of ovarian cancer through the induction of an immune response against Anti-Mullerian Hormone Receptor, Type II (AMHR2).

18 Claims, 23 Drawing Sheets
Specification includes a Sequence Listing.

(56) References Cited

OTHER PUBLICATIONS

Bookman et al., Evaluation of monoclonal humanized anti-HER2 antibody, trastuzumab, in patients with recurrent or refractory ovarian or primary peritoneal carcinoma with overexpression of HER2: a phase II trial of the Gynecologic Oncology Group. Clin Oncol. Jan. 15, 2003;21(2):283-90.
Bos et al., Balancing between Antitumor Efficacy and Autoimmune Pathology in T-Cell-Mediated Targeting of Carcinoembryonic Antigen. Cancer Res. 2008;68(20):8446-55.
Genbank Accession No. AKI72055.1, Jun. 1, 2015, 2 pages.
Genbank Accession No. NM_020547.2, Oct. 7, 2016, 4 pages.
Genbank Accession No. NM_001164690.1, Oct. 6, 2016, 4 pages.
Genbank Accession No. NP_065434, Apr. 9, 2021, 3 pages.
Genbank Accession No. NP_001158163.1, Apr. 9, 2021, 3 pages.
Genbank Accession No. NP_001158162, Apr. 10, 2021, 3 pages.
Gonzalez-Exposito et al., CEA Expression Heterogeneity and Plasticity Confer Resistance to the CEA_Targeting Bispecific Immunotherapy Antibody Cibisatamab (CEA-TCB) in Patient-Derived Colorectal Cancer Orgnoids. J ImmunoTherapy of Cancer. Apr. 15, 2019;7:101.
Kandalaft et al., Immunotherapy for ovarian cancer: what's next? J Clin Oncol. Mar. 1, 2011;29(7):925-33.
Kersual et al., The human Mullerian inhibiting substance type II receptor as immunotherapy target for ovarian cancer: Validation using mAb12G4. MAbs. 2014;6(5):1314-26.
King et al., GM-CSF-dependent, CD103+ dermal dendritic cells play a critical role in Th effector cell differentiation after subcutaneous immunization. J Exp Med. May 10, 2010;207(5):953-61.
Kohlgraf et al., Tumor-specific immunity in MUC1.Tg mice induced by immunization with peptide vaccines from the cytoplasmic tail of CD227 (MUC1). Cancer Immunol Immunother. Dec. 2004;53(12):1068-84.
Mazumder et al., Immunotherapy of Ovarian Cancer with a Monoclonal Antibody Specific for the Extracellular Domain of Anti-Mullerian Hormone Receptor II. Oncotarget. May 19, 2020;11(20)1894-1910.
Mellman et al., Cancer immunotherapy comes of age. Nature. Dec. 21, 2011;480(7378):480-9.
Odunsi et al., NY-ESO-1 and LAGE-1 cancer-testis antigens are potential targets for immunotherapy in epithelial ovarian cancer. Cancer Res. Sep. 15, 2003;63(18):6076-83.
Pardoll, Cancer Vaccines. Immunology Today. Jun. 1993;14(6):310-6.
Rosen et al., Potential markers that complement expression of CA125 in epithelial ovarian cancer. Gynecol Oncol. Nov. 2005;99(2):267-77.
Sakalar et al., Regulation of murine ovarian epithelial carcinoma by vaccination against the cytoplasmic domain of anti-Mullerian hormone receptor II. J Immunol Res. 2015;2015:630287.
Samanci et al., Pharmacological administration of granulocyte/macrophage-colony-stimulating factor is of significant importance for the induction of a strong humoral and cellular response in patients immunized with recombinant carcinoembryonic antigen. Cancer Immunol Immunother. Nov. 1998;47(3):131-42.
Turriziani et al., Carcinoembryonic Antigen (CEA)-Based Cancer Vaccines: Recent Patents and Antitumor Effects from Experimental Models to Clinical Trials. Recent Patents on Anti-Cancer Drug Discovery. May 18, 2012;7(3)265-296.
Ulanova et al., The Common vaccine adjuvant aluminum hydroxide up-regulates accessory properties of human monocytes via an interleukin-4-dependent mechanism. Infect Immun. Feb. 2001;69(2):1151-9.
Ullenhag et al., Functional HLA-DR T cell epitopes of CEA identified in patients with colorectal carcinoma immunized with the recombinant protein CEA. Cancer Immunol Immunother. Apr. 2004;53(4):331-7.
Visser et al., Structure and chromosomal localization of the human anti-müllerian hormone type II receptor gene. Biochem Biophys Res Commun. Oct. 24, 1995;215(3):1029-36.
Zhang et al., Intratumoral T cells, recurrence, and survival in epithelial ovarian cancer. N Engl J Med. Jan. 16, 2003;348(3):203-13.
International Search Report and Written Opinion for International Patent Application PCT/US2016/050159, mailed Dec. 8, 2016, 13 pages.
Kantor, et al., "*Antitumor activity and immune responses induced by a recombinant carcinoembryonic antigen-vaccinia virus vaccine,*" J Natl Cancer Inst.84(14):1084-91 (Jul. 15, 1992).
Lin, et al., "*Treatment of established tumors with a novel vaccine that enhances major histocompatibility class II presentation of tumor antigen,*" Cancer Res.56(1):21-6. PMID: 8548765 (Jan. 1, 1996).

* cited by examiner

Human AMHR2 amino acid sequence, 573 aa variant (SEQ ID NO: 1).

Bold: extracellular domain

*Italics: cytoplasmic domain*

MLGSLGLWALLPTAVEAPPNRRTCVFFEAPGVRGSTKTLGELLDTGTELPRAIRCLYSRC

CFGIWNLTQDRAQVEMQGCRDSDEPGCESLHCDPSPRAHPSPGSTLFTCSCGTDFCNANY

SHLPPPGSPGTPGSQGPQAAPGESIWMALVLLG*LFLLLLLLGSIILALLQRKNYRVRGE*

*PVPEPRPDSGRDWSVELQELPELCFSQVIREGGHAVVWAGQLQGKLVAIKAFPPRSVAQF*

*QAERALYELPGLQHDHIVRFITASRGGPGRLLSGPLLVLELHPKGSLCHYLTQYTSDWGS*

*SLRMALSLAQGLAFLHEERWQNGQYKPGIAHRDLSSQNVLIREDGSCAIGDLGLALVLPG*

*LTQPPAWTPTQPQGPAAIMEAGTQRYMAPELLDKTLDLQDWGMALRRADIYSLALLLWEI*

*LSRCPDLRPDSSPPPFQLAYEAELGNTPTSDELWALAVQERRRPYIPSTWRCFATDPDGL*

*RELLEDCWDADPEARLTAECVQQRLAALAHPQESHPFPESCPRGCPPLCPEDCTSIPAPT*

*ILPCRPQRSACHFSVQQGPCSRNPQPACTLSPV*

OVARIAN CANCER VACCINES

CROSS REFERENCE TO RELATED APPLICATIONS

This application is a continuation of U.S. patent application Ser. No. 15/757,151, filed Mar. 2, 2018, now U.S. Pat. No. 11,090,284, which claims the benefit of priority to U.S. Provisional Patent Application No. 62/213,286, filed Sep. 2, 2015, each of which is hereby incorporated by reference in its entirety.

GOVERNMENT RIGHTS

This invention was made with government support under CA140350 awarded by the National Institutes of Health. The government has certain rights in the invention.

SEQUENCE LISTING

The text of the computer readable sequence listing filed herewith, titled "39521-304_SEQUENCE_LISTING", created on Sep. 7, 2023, and having a file size of 29,705 bytes, is hereby incorporated by reference in its entirety.

BACKGROUND

Epithelial ovarian cancer (EOC) is the leading cause of death from gynecologic malignancies in the United States. Approximately 60% of ovarian cancers are diagnosed at late stages, and although initial responses to the current standard of care are high, most patients have disease recurrence resulting in a five year overall survival (OS) rate slightly over 45%.

Induction of ovarian tumor immunity through vaccination is a promising approach, the potential efficacy of which is supported by the increased OS observed in patients whose ovarian tumors are infiltrated by T cells. Therapeutic ovarian cancer vaccine strategies using whole tumor homogenate or certain tumor associated antigens, such as human epidermal growth factor receptor 2 (HER2), cancer-testis antigen 1 (CTAG1B or NY-ESO-1), and cancer antigen 25 (CA-125) have been attempted, but have provided only modest therapeutic results (Zhang et al., *Journal of Medicine* 348:203-213 (2003); Kandalaft et al., *Journal of Clinical Oncology* 29:925-933 (2011); Bookman et al., *Journal of Clinical Oncology* 21:283-290 (2003); Odunsi et al., *Cancer Research* 63:6076-6083 (2004); and Rosen et al., *Gynecologic Oncology* 99:267-277 (2005), each of which is hereby incorporated by reference in its entirety).

Thus, considering the high rate of ovarian cancer recurrence and the low five year survival rate, there is great need for new compositions and methods for the treatment and prevention of ovarian cancer.

SUMMARY

In certain aspects, provided herein are methods and compositions for the treatment and/or prevention of ovarian cancer through the induction of an immune response against Anti-Mullerian Hormone Receptor, Type II (AMHR2).

In certain aspects, provided herein is a method of treating an ovarian cancer tumor (e.g., a primary or metastatic ovarian cancer, such as an epithelial ovarian cancer tumor) in a subject (e.g., a female human subject) comprising administering to the subject an immunogenic composition comprising a polypeptide (i.e., an "AMHR2 polypeptide") having an amino acid sequence that includes at least a portion of the amino acid sequence of an AMHR2 protein (e.g., at least a portion of SEQ ID NO: 1), a nucleic acid encoding an AMHR2 polypeptide, an antigen-presenting cell presenting an AMHR2 epitope, and/or an AMHR2-primed lymphocyte (e.g., a T lymphocyte and/or a B lymphocyte). In some embodiments, the ovarian cancer tumor expresses AMHR2. In some embodiments, administration of the immunogenic composition induces an immune response against the ovarian cancer tumor in the subject (e.g., a T cell immune response, such as a type 1 and/or type 17 immune response and/or a B cell immune response, such as an IgG response). In some embodiments, the subject is administered multiple doses of the immunogenic composition (e.g., at least 2, 3, 4, 5 or 6 doses). In some embodiments, the subject has undergone surgery to remove at least part of the ovarian cancer tumor. In some embodiments, the method further comprises the step of surgically removing at least part of the ovarian cancer tumor.

In certain aspects, provided herein is a method of preventing ovarian cancer and/or preventing recurrence of ovarian cancer in a subject (e.g., a female human subject) comprising administering to the subject an immunogenic composition comprising a polypeptide (i.e., an "AMHR2 polypeptide") having an amino acid sequence that includes at least a portion of the amino acid sequence of an AMHR2 protein (e.g., SEQ ID NO: 1), a nucleic acid encoding an AMHR2 polypeptide, an antigen-presenting cell presenting an AMHR2 epitope, and/or an AMHR2-primed lymphocyte (e.g., a T lymphocyte and/or a B lymphocyte). In some embodiments, administration of the immunogenic composition induces an immune response against the AMHR2 in the subject (e.g., a T cell immune response, such as a type 1 and/or type 17 immune response and/or a B cell immune response, such as an IgG response). In some embodiments, the subject is administered multiple doses of the immunogenic composition (e.g., at least 2, 3, 4, 5 or 6 doses). In some embodiments, the subject has undergone surgery to remove at least part of an ovarian cancer tumor e.g., an ovarian cancer tumor expresses AMHR2, such as a primary or metastatic ovarian cancer tumor). In some embodiments, the tumor is an epithelial ovarian cancer tumor. In some embodiments, the method further comprises the step of surgically removing at least part of the ovarian cancer tumor.

In some embodiments of the methods provided herein, the immunogenic composition comprises an adjuvant. In some embodiments, the adjuvant is Adjuvant 65, α-GalCer, aluminum phosphate, aluminum hydroxide, calcium phosphate, β-Glucan Peptide, CpG DNA, GM-CSF, GPI-0100, IFA, IFN-7, IL-17, lipid A, lipopolysaccharide, Lipovant, Montanide, N-acetyl-muramyl-L-alanyl-D-isoglutamine, Pam3CSK4, poly-IC, quil A, trehalose dimycolate, or zymosan. In some embodiments, the adjuvant is one that induces a mixed type 1/type 17 immune response.

In some embodiments of the methods provided herein, the method further comprises the step of determining whether an ovarian cancer tumor in the subject and/or from the subject expresses AMHR2. In some embodiments, the methods include the step of testing a tumor sample obtained from the subject for expression of AMHR2. In some embodiments, expression of AMHR2 is determined by detecting the presence of AMHR2 protein in the tumor sample (e.g. by FACS, fluorescent microscopy, western blot, etc.). In some embodiments, the AMHR2 protein is detected by contacting the sample with a detectably labeled antibody (e.g., an antibody directly or indirectly labeled with a fluorescent moiety). In some embodiments, expression of AMHR2 is determined by detecting the presence of AMHR2 mRNA (e.g., by RT-PCR, northern blot, etc.). In some embodiments, the AMHR2 mRNA is detected by contacting the sample with a detectably labeled nucleic acid probe (e.g., a probe directly or indirectly labeled with a fluorescent moiety). In some embodiments, the method comprised obtaining the sample from the subject (e.g., by tumor biopsy).

In some embodiments of the methods provided herein, the method further comprises the step of determining whether the administration of the immunogenic composition induces an immune response against the ovarian cancer tumor and/or AMHR2 in the subject. In some embodiments, the immune response is a T cell immune response (e.g., a mixed type 1/type 17 immune response). In some embodiments, the immune response is detected by detecting the presence of cytokines (e.g., IFN-7 and/or IL-17) in a patient sample (e.g., a patient serum sample). In some embodiments, the cytokines are detected by contacting the sample with, directly or indirectly, detectably labeled antibodies specific for the cytokines to be detected. In some embodiments, the cytokines are detected by performing an ELISA assay. In some embodiments, the immune response is a B cell immune response. In some embodiments, the B cell immune response is detected by detecting the presence of anti-AMHR2 antibodies e.g., anti-AMHR2 IgG antibodies) in a patient sample (e.g., a serum sample).

In certain embodiments, the methods provided herein further comprise the step of administering an additional agent to the subject. In some embodiments, the additional agent is an anti-cancer agent. In some embodiments, the anti-cancer agent is paclitaxel, cisplatin, topotecan, gemcitabine, bleomycin, etoposide, carboplatin, docetaxel, doxorubicin, topotecan, cyclophosphamide, trabectedin, olaparib, tamoxifen, letrozole or bevacizumab. In some embodiments, the anti-cancer agent is an immune checkpoint inhibitor. In some embodiments, the immune checkpoint inhibitor is an inhibitor of CTLA4, such as an anti-CTLA4 antibody (e.g., ipilimumab (BMS), tremelimumab (AstraZeneca) and/or KAHR-102 (Kahr Medical)). In some embodiments, the immune checkpoint inhibitor is an inhibitor of PD-1, such as an anti-PD-1 antibody (e.g., nivolumab (BMS), pembrolizumab/lambrolizumab (Merck), pidilizumab (Curetech), AMP-224 (GSK), AMP-514 (AstraZeneca), STI-A1110 (Sorrento) and/or TSR-042 (Tesaro). In some embodiments, the immune checkpoint inhibitor is an inhibitor of PD-L1 and/or PD-L2, such as an anti-PD-L1 and/or an anti-PD-L2 antibody (e.g., RG-7446 (Roche), BMS-936559 (BMS), MEDI-4736 (AstraZeneca), MSB-0020718C (Merck), AUR-012 (Pierre Fabre Med), STI-A1010 (Sorrento)).

In certain embodiments of the methods provided herein, the human female subject is predisposed to ovarian cancer. In some embodiments, the genome of the subject comprises a BRCA1 or BRCA2 mutation that predisposes the subject to ovarian cancer. In some embodiments, the subject has a family history of ovarian cancer. In some embodiments, the subject is a post-menopausal human female.

In certain aspects, provided herein is a kit and/or a composition (e.g., an immunogenic composition) for preventing and/or treating ovarian cancer in a subject (e.g., a female human subject), the kit or composition comprising a polypeptide (i.e., an "AMHR2 polypeptide") having an amino acid sequence that includes at least a portion of the amino acid sequence of an AMHR2 protein (e.g., SEQ ID NO: 1), a nucleic acid encoding an AMHR2 polypeptide, an antigen-presenting cell presenting an AMHR2 epitope, and/or an AMHR2-primed lymphocyte (e.g., a T lymphocyte and/or a B lymphocyte). In some embodiments, the kit comprises multiple doses of the polypeptide, nucleic acid, antigen presenting cell and/or lymphocyte. In some embodiments, the kit further comprises instructions for use.

In certain embodiments of the kits and compositions provided herein, the kit or composition further comprises an adjuvant. In some embodiments, the adjuvant is Adjuvant 65, α-GalCer, aluminum phosphate, aluminum hydroxide, calcium phosphate, β-Glucan Peptide, CpG DNA, GM-CSF, GPI-0100, IFA, IFN-7, IL-17, lipid A, lipopolysaccharide, Lipovant, Montanide, N-acetyl-muramyl-L-alanyl-D-isoglutamine, Pam3CSK4, quil A, trehalose dimycolate or zymosan. In some embodiments, adjuvant is one that induces a mixed type 1/type 17 immune response.

In some embodiments of the kits or compositions provided herein, the kit or composition further comprises an additional agent (e.g., an anti-cancer agent). In some embodiments, the additional agent is an anti-cancer agent selected from the group consisting of paclitaxel, cisplatin, topotecan, gemcitabine, bleomycin, etoposide, carboplatin, docetaxel, doxorubicin, topotecan, cyclophosphamide, trabectedin, olaparib, tamoxifen, letrozole and bevacizumab.

In some embodiments, the anti-cancer agent is an immune checkpoint inhibitor. In some embodiments, the immune checkpoint inhibitor is an inhibitor of CTLA4, such as an anti-CTLA4 antibody (e.g., ipilimumab (BMS), tremelimumab (AstraZeneca) and/or KAHR-102 (Kahr Medical)). In some embodiments, the immune checkpoint inhibitor is an inhibitor of PD-1, such as an anti-PD-1 antibody (e.g., nivolumab (BMS), pembrolizumab/lambrolizumab (Merck), pidilizumab (Curetech), AMP-224 (GSK), AMP-514 (AstraZeneca), STI-A1110 (Sorrento) and/or TSR-042 (Tesaro). In some embodiments, the immune checkpoint inhibitor is an inhibitor of PD-L1 and/or PD-L2, such as an anti-PD-L1 and/or an anti-PD-L2 antibody (e.g., RG-7446 (Roche), BMS-936559 (BMS), MEDI-4736 (AstraZeneca), MSB-0020718C (Merck), AUR-012 (Pierre Fabre Med), STI-A1010 (Sorrento)).

BRIEF DESCRIPTION OF THE DRAWINGS

FIG. 19 is the amino acid sequence of the longest of the human AMHR2-CD protein variant (SEQ ID NO: 1). The extracellular domain (AMHR2-ED) is indicated in bold and the cytoplasmic domain (AMHR2-CD) is indicated in italics.

Figure 1:
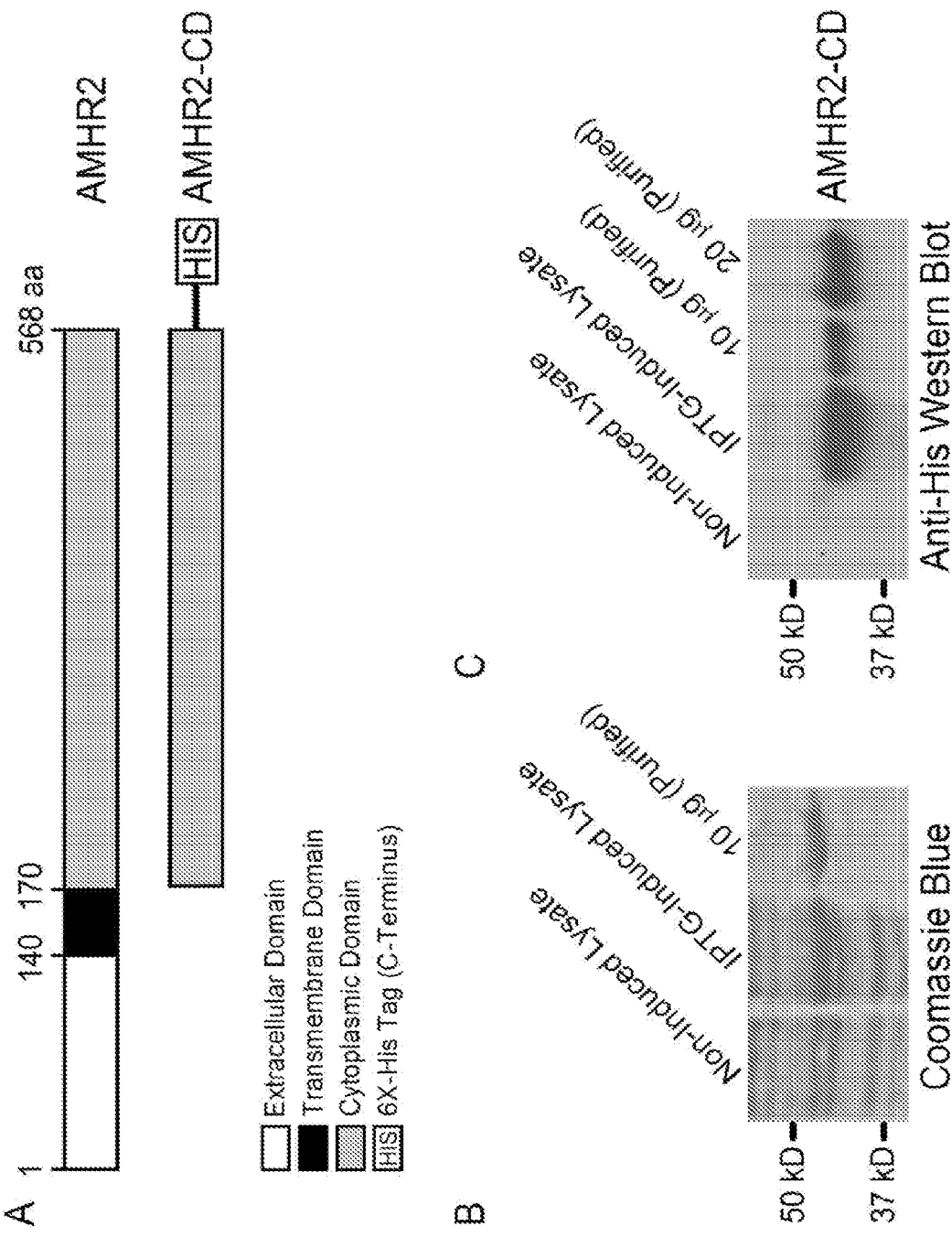
FIG. 1 has three panels. Panel (A) is a schematic representation of full length AMHR2 showing the extracellular, transmembrane, and cytoplasmic domains with a C-terminal 6×His-tagged AMHR2-CD variant. Panel (B) depicts an SDS-PAGE gel stained with Coomassie blue showing expression of AMHR2-CD in non-induced, IPTG-induced, and Ni-NTA affinity purified AMHR2-CD. Panel (C) depicts an anti-His Western blot of an SDS-PAGE gel showing expression of AMHR2-CD in non-induced, IPTG-induced, and two doses of Ni-NTA affinity purified AMHR2-CD.

Panel (E) shows transfer of affinity purified IgG from AMHR2-ED immunized mice into TgMISIIR-TAg (low) female mice one day prior to MOVCAR inoculation resulted in significant inhibition of tumor growth and panel (F) shows enhanced overall survival compared to mice receiving affinity purified IgG from ovalbumin immunized mice. In all cases, error bars indicate ±SD, and asterisks indicate significance.

DETAILED DESCRIPTION

General

Provided herein are methods, kits and compositions for the treatment and/or prevention of ovarian cancer through the induction of an immune response against Anti-Mullerian Hormone Receptor, Type II (AMHR2).

AMHR2 is a serine/threonine kinase receptor homologous to type II receptors of the transforming growth factor beta (TGFβ) family. The human AMHR2 gene contains 11 exons with seven known alternatively spliced variants producing three known coded proteins, one additional variant with protein coding features, and three non-coding transcripts with no open reading frames. In adult women, the longest human protein coding transcript for a 573 amino acid long protein (SEQ ID NO: 1; FIG. 19) is normally expressed only in the ovary and comprises a 127 amino acid extracellular domain (AMHR2-ED), a 26 amino acid transmembrane domain, and a 403 amino acid cytoplasmic domain (AMHR2-CD). AMHR2 signaling causes regression of the Müllerian ducts during male development and regulates oocyte development and follicle production in adult females, thereby providing substantial control of ovarian reserve and fertility. AMHR2 is expressed in the vast majority of human EOCs, including 90% of primary EOCs, 78% of borderline malignancies, 77-86% of non-EOC ovarian tumors, and 56% of malignant ascites from grade III-IV ovarian cancers. In normal tissues, AM R2-CD expression is predominantly confined to the ovaries. While some AMHR2-CD expression also occurs in a small number of additional human tissues, AMHR2-ED is expressed exclusively in the ovary. What is more, ovarian expression of both AMHR2-CD and AMHR2-ED is reduced in post-menopausal ovaries.

As described herein, vaccination with AMHR2 polypeptides and/or adoptive transfer of AMHR2-primed lymphocytes provides effective immunotherapy against ovarian cancer without producing extensive autoimmune complications. Immunization of a mouse model for ovarian cancer with either recombinant mouse AMHR2 polypeptides containing either a 399 amino acid sequence of the cytoplasmic domain (AMHR2-CD) or a 140 amino acid sequence of the extracellular domain (AMHR2-ED) resulted in a prominent proinflammatory T cell response accompanied by extremely high IgG antibody titers.

Vaccination with AMHR2-CD and AMHR2-ED polypeptides provided significant T cell-mediated prophylaxis and therapy against ovarian cancer and mediated significant prophylaxis against the development of autochthonous ovarian cancer tumors in the mouse ovarian cancer models. Moreover, the protection against tumor growth was accompanied by minimal autoimmune symptoms, with no detectable effects on fertility over the course of several subsequent mating cycles. These data indicate that targeted vaccination against AMHR2-CD and/or AMHR2-ED provides a safe and effective therapy against ovarian cancer.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

The term "immune response" refers herein to any response to an antigen or antigenic determinant by the immune system. Exemplary immune responses include humoral immune responses (e.g. production of antigen-specific antibodies (neutralizing or otherwise)) and cell-mediated immune responses (e.g. lymphocyte proliferation). Type-1 inflammatory immune responses are characterized by the production of type-1 cytokines, such as IFNγ. Type-2 inflammatory immune responses are characterized by expression of type-2 cytokines, such as IL-4 or IL-5. Type-17 inflammatory immune responses are characterized by expression of type-17 cytokines, and particularly IL-17. In some instances, a mixed immune response can be generated. For example, in some instances a mixed type-1/type-17 inflammatory immune response is generated that is characterized by the expression of both IFNγ and IL-17.

As used herein, "percent identity" between amino acid sequences is synonymous with "percent homology," which can be determined using the algorithm of Karlin and Altschul (*Proc. Natl. Acad. Sci. USA* 87, 2264-2268, 1990), modified by Karlin and Altschul (*Proc. Natl. Acad. Sci. USA* 90, 5873-5877, 1993). The noted algorithm is incorporated into the NBLAST and XBLAST programs of Altschul et al. (*J. Mol. Biol.* 215, 403-410, 1990). BLAST nucleotide searches are performed with the NBLAST program score=100, wordlength=12, to obtain nucleotide sequences homologous to a polynucleotide described herein. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (*Nucleic Acids Res.* 25, 3389-3402, 1997). When utilizing BLAST and Gapped BLAST programs, the default parameters of the respective programs (e.g., XBLAST and NBLAST) are used.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

Anti-Mullerian Hormone Receptor II (AMHR2)

In certain aspects, provided herein are provided herein are methods, kits and compositions for the treatment and/or prevention of ovarian cancer through the induction of an immune response against Anti-Mullerian Hormone Receptor, Type II (AMHR2) through the administration of an AMHR2 polypeptide (e.g., a polypeptide containing the AMHR2-ED or an immunogenic fragment thereof, or the AMHR2-CD or an immunogenic fragment thereof) or a nucleic acid encoding an AMHR2 polypeptide.

The human AMHR2 gene contains 11 exons with seven known alternatively spliced variants producing three known coded proteins, one additional variant with protein coding features, and three non-coding transcripts with no open reading frames. In adult women, the longest human protein coding transcript for a 573 amino acid long protein is normally expressed only in the ovary and comprises a 127 amino acid extracellular domain, a 26 amino acid transmembrane domain, and a 403 amino acid cytoplasmic domain (FIG. 19). AMHR2 signaling causes regression of the Müllerian ducts during male development and regulates oocyte development and follicle production in adult females, thereby providing substantial control of ovarian reserve and fertility. The mRNA sequences of the three protein-coding isoforms of AMHR2 are provided at NCBI reference numbers NM_020547.2, NM_001164690.1 and NM_001164690.1, which encode for proteins having amino acid sequences provided at NCBI reference numbers NP_065434.1, NP_001158162.1 and NP_001158163.1, respectively. Each of the above mRNA and protein sequences are hereby incorporated by reference.

In some embodiments, provided herein are AMHR2 polypeptides and/or nucleic acids encoding AMHR2 polypeptides. AMHR2 polypeptides are polypeptides that include an amino acid sequence that corresponds to the amino acid sequence of an AMHR2 protein, the AMHR2-ED, the AMHR2-CD, and/or a portion of the AMHR2 amino acid sequence of sufficient length to elicit an AMHR2-specific immune response. In certain embodiments, the AMHR2 polypeptide also includes amino acids that do not correspond to the amino acid sequence (e.g., a fusion protein comprising an AMHR2 amino acid sequence and an amino acid sequence corresponding to a non-AMHR2 protein or polypeptide). In some embodiments, the AMHR2 polypeptide only includes amino acid sequence corresponding to an AMHR2 protein or fragment thereof.

In certain embodiments of the methods, compositions and kits provided herein, the AMHR2 polypeptide has an amino acid sequence that comprises at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 140, 150, 160, 170, 180, 190 or 200 consecutive amino acids of an AMHR2 protein amino acid sequence. In some embodiments, the consecutive amino acids are identical to an amino acid sequence in the cytoplasmic domain of AMHR2. In some embodiments, the consecutive amino acids are identical to an amino acid sequence in the extracellular domain of AMHR2.

In certain embodiments of the methods provided herein, the AMHR2 polypeptide has an amino acid sequence that consists essentially of at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 140, 150, 160, 170, 180, 190 or 200 consecutive amino acids of an AMHR2 protein amino acid sequence. In some embodiments, the consecutive amino acids are identical to an amino acid sequence in the cytoplasmic domain of AMHR2. In some embodiments, the consecutive amino acids are identical to an amino acid sequence in the extracellular domain of AMHR2.

In certain embodiments of the methods provided herein, the AMHR2 polypeptide has an amino acid sequence that consists of at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 140, 150, 160, 170, 180, 190 or 200 consecutive amino acids of an AMHR2 protein amino acid sequence. In some embodiments, the consecutive amino acids are identical to an amino acid sequence in the cytoplasmic domain of AMHR2. In some embodiments, the consecutive amino acids are identical to an amino acid sequence in the extracellular domain of AMHR2.

In some embodiments of the methods provided herein, the AMHR2 polypeptide has an amino acid sequence that comprises 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 140, 150, 160, 170, 180, 190 or 200 consecutive amino acids that are at least 70%, 75%, 80%, 85%, 90%, 91%, 92%, 93%, 94%, 95%, 96%, 77%, 98% or 99% identical to an amino acid sequence in an AMHR2 protein. In some embodiments, the amino acid sequence is in the cytoplasmic domain of an AMHR2 protein. In some embodiments, the amino acid sequence is in the extracellular domain of an AMHR2 protein.

In some embodiments of the methods provided herein, the AMHR2 polypeptide has an amino acid sequence that consists essentially of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 140, 150, 160, 170, 180, 190 or 200 consecutive amino acids that are at least 70%, 75%, 80%, 85%, 90%, 91%, 92%, 93%, 94%, 95%, 96%, 77%, 98% or 99% identical to an amino acid sequence in an AMHR2 protein. In some embodiments, the amino acid sequence is in the cytoplasmic domain of an AMHR2 protein. In some embodiments, the amino acid sequence is in the extracellular domain of an AMHR2 protein.

In some embodiments of the methods, compositions and kits provided herein, the AMHR2 polypeptide has an amino acid sequence that consists of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 140, 150, 160, 170, 180, 190 or 200 consecutive amino acids that are at least 70%, 75%, 80%, 85%, 90%, 91%, 92%, 93%, 94%, 95%, 96%, 77%, 98% or 99% identical to an amino acid sequence in an AMHR2 protein. In some embodiments, the amino acid sequence is in the cytoplasmic domain of an AMHR2 protein. In some embodiments, the amino acid sequence is in the extracellular domain of an AMHR2 protein.

In some embodiments of the methods, compositions and kits provided herein, the AMHR2 polypeptide does not comprise an amino acid sequence identical to the extracellular domain of AMHR2. In some embodiments, the AMHR2 polypeptide does not comprise an amino acid sequence identical to the transmembrane domain of AMHR2. In some embodiments, the AMHR2 polypeptide does not comprise an amino acid sequence identical to the cytoplasmic domain of AMHR2.

As is well-known to those skilled in the art, polypeptides having substantial sequence similarities can cause identical or very similar immune reaction in a host animal. Accordingly, in some embodiments, a derivative, equivalent, variant, fragment, or mutant of AMHR2 protein or fragment thereof can also suitable for the methods, compositions and kits provided herein.

In some embodiments, variations or derivatives of the AMHR2 polypeptides are provided herein. The altered polypeptide may have an altered amino acid sequence, for example by conservative substitution, yet still elicits immune responses which react with the unaltered protein antigen, and are considered functional equivalents. As used herein, the term "conservative substitution" denotes the replacement of an amino acid residue by another, biologically similar residue. It is well known in the art that the amino acids within the same conservative group can typically substitute for one another without substantially affecting the function of a protein. According to certain embodiments, the derivative, equivalents, variants, or mutants of the ligand-binding domain of an AMHR2 polypeptide are polypeptides that are at least 85% homologous a sequence of the AMHR2 protein or fragment thereof. In some embodiments, the homology is at least 90%, at least 95%, or at least 98%.

In some embodiments, provided herein is a nucleic acid encoding an AMHR2 polypeptide described herein, such as a DNA molecule encoding an AMHR2 polypeptide. In some embodiments the composition comprises an expression vector comprising an open reading frame encoding an AMHR2 polypeptide. In some embodiments, the AMHR2 nucleic acid includes regulatory elements necessary for expression of the open reading frame. Such elements can include, for example, a promoter, an initiation codon, a stop codon, and a polyadenylation signal. In addition, enhancers can be included. These elements can be operably linked to a sequence that encodes the AMHR2 polypeptide.

Examples of promoters include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein. Examples of suitable polyadenylation signals include but are not limited to SV40 polyadenylation signals and LTR polyadenylation signals.

In addition to the regulatory elements required for expression, other elements may also be included in the nucleic acid molecule. Such additional elements include enhancers. Enhancers include the promoters described hereinabove. Preferred enhancers/promoters include, for example, human actin, human myosin, human hemoglobin, human muscle creatine and viral enhancers such as those from CMV, RSV and EBV.

In some embodiments, the nucleic acid can be operably incorporated in a carrier or delivery vector. Useful delivery vectors include but are not limited to biodegradable microcapsules, immuno-stimulating complexes (ISCOMs) or liposomes, and genetically engineered attenuated live carriers such as viruses or bacteria.

In some embodiments, the vector is a viral vector, such as lentiviruses, retroviruses, herpes viruses, adenoviruses, adeno-associated viruses, vaccinia viruses, baculoviruses, Fowl pox, AV-pox, modified vaccinia Ankara (MVA) and other recombinant viruses. For example, a vaccinia virus vector can be used to infect dendritic cells.

Pharmaceutical Compositions

In certain aspects, provided herein are pharmaceutical compositions (e.g., a vaccine composition) comprising an AMHR2 polypeptide described herein and/or a nucleic acid encoding an AMHR2 polypeptide described herein. In some embodiments, the composition comprises a pharmaceutically acceptable carrier. In some embodiments, the composition includes a combination of multiple e.g., two or more) AMHR2 polypeptides or nucleic acids described herein.

The pharmaceutical compositions disclosed herein may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous or epidural injection as, for example, a sterile solution or suspension, or sustained-release formulation.

Methods of preparing these formulations or compositions include the step of bringing into association an AMHR2 polypeptide and/or nucleic acid described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions suitable for parenteral administration comprise AMHR2 polypeptides and/or nucleic acids described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Regardless of the route of administration selected, the agents provided herein, which may be used in a suitable hydrated form, and/or the pharmaceutical compositions disclosed herein, are formulated into pharmaceutically-acceptable dosage forms by conventional methods known to those of skill in the art.

In some embodiments, the pharmaceutical composition described, when administered to a subject, can elicit an immune response against a cell that expresses AMHR2. Such pharmaceutical compositions can be useful as vaccine compositions for prophylactic and/or therapeutic treatment of ovarian cancer.

In some embodiments, the pharmaceutical composition further comprises a physiologically acceptable adjuvant. In some embodiments, the adjuvant employed provides for increased immunogenicity of the pharmaceutical composition. The adjuvant can be one that provides for slow release of antigen (e.g., the adjuvant can be a liposome), or it can be an adjuvant that is immunogenic in its own right thereby functioning synergistically with antigens (i.e., antigens present in the AMHR2 polypeptide). For example, the adjuvant can be a known adjuvant or other substance that promotes antigen uptake, recruits immune system cells to the site of administration, or facilitates the immune activation of responding lymphoid cells. Adjuvants include, but are not limited to, immunomodulatory molecules (e.g., cytokines), oil and water emulsions, aluminum hydroxide, glucan, dextran sulfate, iron oxide, sodium alginate, Bacto-Adjuvant, synthetic polymers such as poly amino acids and co-polymers of amino acids, saponin, paraffin oil, and muramyl dipeptide. In some embodiments, the adjuvant is Adjuvant 65, α-GalCer, aluminum phosphate, aluminum hydroxide, calcium phosphate, β-Glucan Peptide, CpG DNA, GM-CSF, GPI-0100, IFA, IFN-7, IL-17, lipid A, lipopolysaccharide, Lipovant, Montanide, N-acetyl-muramyl-L-alanyl-D-isoglutamine, Pam3CSK4, quil A, trehalose dimycolate or zymosan. In some embodiments, adjuvant is one that induces a mixed type 1/type 17 immune response.

In some embodiments, the adjuvant is an immunomodulatory molecule. For example, the immunomodulatory molecule can be a recombinant protein cytokine, chemokine, or immunostimulatory agent or nucleic acid encoding cytokines, chemokines, or immunostimulatory agents designed to enhance the immunologic response.

Examples of immunomodulatory cytokines include interferons (e.g., IFNα, IFNβ and IFNγ), interleukins (e.g., IL-1, IL-2, IL-3, IL-4, IL-5, IL-6, IL-7, IL-8, IL-9, IL-10, IL-12, IL-17 and IL-20), tumor necrosis factors (e.g., TNFα and TNFβ), erythropoietin (EPO), FLT-3 ligand, gIp10, TCA-3, MCP-1, MIF, MIP-1.alpha., MIP-1β, Rantes, macrophage colony stimulating factor (M-CSF), granulocyte colony stimulating factor (G-CSF), and granulocyte-macrophage colony stimulating factor (GM-CSF), as well as functional fragments of any of the foregoing.

In some embodiments, an immunomodulatory chemokine that binds to a chemokine receptor, i.e., a CXC, CC, C, or CX3C chemokine receptor, also can be included in the compositions provided here. Examples of chemokines include, but are not limited to, Mip1α, Mip-1β, Mip-3α (Larc), Mip-3β, Rantes, Hcc-1, Mpif-1, Mpif-2, Mcp-1, Mcp-2, Mcp-3, Mcp-4, Mcp-5, Eotaxin, Tarc, Elc, 1309, IL-8, Gcp-2 Gro-α, Gro-β, Gro-γ, Nap-2, Ena-78, Gcp-2, Ip-10, Mig, I-Tac, Sdf-1, and Bca-1 (Blc), as well as functional fragments of any of the foregoing.

In certain embodiments, compositions provided herein also comprise one or more other agents such as, but not limited to, chemotherapeutic, immunotherapeutic, immunomodulatory and/or anti-angiogenic agents.

In some embodiments, the one or more other agents can be a chemotherapeutic agent, naturally occurring or synthetic, for example as described in "Cancer Chemotherapeutic Agents", American Chemical Society, 1995, W. O. Foye Ed.

In one embodiment, the chemotherapeutic agent is selected from the group consisting of a small molecule receptor antagonists such as vatalanib, SU 11248 or AZD-6474, EGFR or HER2 antagonists such as gefitinib, erlotinib, CI-1033 or Herceptin, antibodies such as bevacizumab, cetuximab, rituximab, DNA alkylating drugs such as cisplatin, oxaliplatin or carboplatin, anthracyclines such as doxorubicin or epirubicin, an antimetabolite such as 5-FU, pemetrexed, gemcitabine or capecitabine, a camptothecin such as irinotecan or topotecan, an anti-cancer drug such as paclitaxel or docetaxel, an epipodophyllotoxin such as etoposide or teniposide, a proteasome inhibitor such as bortezomib or anti-inflammatory drugs such as celecoxib or rofecoxib, optionally in form of the pharmaceutically acceptable salts, in form of the hydrates and/or solvates and optionally in the form of the individual optical isomers, mixtures of the individual enantiomers or racemates thereof.

In another embodiment, the chemotherapeutic agent is selected from the group consisting of a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/IER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenyl)amino]-6-{[4-(N,N-dimethylamino)-1-oxo-2-bute-n-1-yl]amino}-7-((S)-tetrahydrofuran-3-yloxy)quinazoline or 4-[(3-chloro-4-fluoro-phenyl)amino]-6-{[4-(homomorpholin-4-yl)-1-oxo-2-bu- -ten-1-yl]amino}-7-[(S)-(tetrahydrofuran-3-yl)oxy]-quinazoline, or a pharmaceutically acceptable salt thereof, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, an anti-cancer drug from plants such as paclitaxel (taxol), docetaxel or taxotere, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as bortezomib, an enzyme such as asparaginase, pegylated asparaginase (pegaspargase) or a thymidine-phosphorylase inhibitor, a gestagen or an estrogen such as estramustine (T-66) or megestrol, an anti-androgen such as flutamide, casodex, anandron or cyproterone acetate, an aromatase inhibitor such as aminogluthetimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17.beta.-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon .beta., an interleukin such as IL-10 or IL-12, an anti-TNF.alpha. antibody such as etanercept, an immunomodulatory drug such as thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody, a tolerance induction agent, a biphosphonate or derivative thereof such as minodronic acid or its derivatives (YM-529, Ono-5920, YH-529), zoledronic acid monohydrate, ibandronate sodium hydrate or clodronate disodium, a nitroimidazole such as metronidazole, misonidazole, benznidazole or nimorazole, a nitroaryl compound such as RSU-1069, a nitroxyl or N-oxide such as SR-4233, an halogenated pyrimidine analogue such as bromodeoxyuridine, iododeoxyuridine, a thiophosphate such as WR-272 1, a photochemically activated drug such as porfimer, photofrin, a benzoporphyrin derivative, a pheophorbide derivative, merocyanin 540 (MC-540) or tin etioporpurin, an anttemplate or an anti-sense RNA or DNA such as oblimersen, a non-steroidal inflammatory drug such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lomoxicam, nimesulide, meloxicam, celecoxib, rofecoxib, or a pharmaceutically acceptable salt of a nonsteroidal inflammatory drug, a cytotoxic antibiotic, an antibody targeting the surface molecules of cancer cells such as apolizumab or 1D09C3, an inhibitor of metalloproteinases such as TIMP-1 or TIMP-2, Zinc, an inhibitor of oncogenes such as P53 and Rb, a complex of rare earth elements such as the heterocyclic complexes of lanthanides, a photochemotherapeutic agent such as PUVA, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, or a therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamoxifen and testolactone. Preferred compounds include small molecule VEGF receptor antagonist such as vatalanib (PTK-787/ZK222584), SU-5416, SU-6668, SU-11248, SU-14813, AZD-6474, EGFR/HER2 antagonists such as CI-1033 or GW-2016, an EGFR antagonist such as iressa (gefitinib, ZD-1839), tarceva (erlotinib, OSI-774), PKI-166, EKB-569, HKI-272 or herceptin, an antagonist of the mitogen-activated protein kinase such as BAY-43-9006 or BAY-57-9006, atrasentan, rituximab, cetuximab, Avastin™ (bevacizumab), IMC-1C11, erbitux (C-225), DC-101, EMD-72000, vitaxin, imatinib, an alkylating agent or a platinum compound such as melphalan, cyclophosphamide, cisplatin, carboplatin, oxaliplatin, satraplatin, daunorubicin, doxorubicin (adriamycin), liposomal doxorubicin (doxil), epirubicin, idarubicin, a pyrimidine or purine analogue or antagonist or an inhibitor of the nucleoside diphosphate reductase such as cytarabine, 5-fluorouracile (5-FU), pemetrexed, tegafur/uracil, gemcitabine, capecitabine, mercaptopurine, methotrexate, an anticancer drug such as paclitaxel (taxol) or docetaxel, a vinca alkaloid such as navelbine, vinblastin, vincristin, vindesine or vinorelbine, an antimitotic peptide such as dolastatin, an epipodophyllotoxin or a derivative of podophyllotoxin such as etoposide or teniposide, a non-steroidal inflammatory drug such as meloxicam, celecoxib, rofecoxib, an antibody targeting the surface molecules of cancer cells such as apolizumab or ID09C3 or the heat shock protein HSP90 modulator geldanamycin and its derivative 17-allylaminogeldanamycin or 17-AAG.

In another embodiment, the chemotherapeutic agent is selected from the group consisting of compounds interacting with or binding tubulin, synthetic small molecule VEGF receptor antagonists, small molecule growth factor receptor antagonists, inhibitors of the EGF receptor and/or VEGF receptor and/or integrin receptors or any other protein tyrosine kinase receptors which are not classified under the synthetic small-molecules, inhibitors directed to EGF receptor and/or VEGF receptor and/or integrin receptors or any other protein tyrosine kinase receptors, which are fusion proteins, compounds which interact with nucleic acids, and which are classified as alkylating agents or platinum compounds, compounds which interact with nucleic acids and which are classified as anthracyclines, as DNA intercalators or as DNA cross-linking agents, including DNA minorgroove binding compounds, anti-metabolites, naturally occurring, semi-synthetic or synthetic bleomycin type antibiotics, inhibitors of DNA transcribing enzymes, and especially the topoisomerase I or topoisomerase II inhibitors, chromatin modifying agents, mitosis inhibitors, anti-mitotic agents, cell-cycle inhibitors, proteasome inhibitors, enzymes, hormones, hormone antagonists, hormone inhibitors, inhibitors of steroid biosynthesis, steroids, cytokines, hypoxia-selective cytotoxins, inhibitors of cytokines, lymphokines, antibodies directed against cytokines, oral and parenteral tolerance induction agents, supportive agents, chemical radiation sensitizers and protectors, photo-chemically activated drugs, synthetic poly- or oligonucleotides, optionally modified or conjugated, non-steroidal anti-inflammatory drugs, cytotoxic antibiotics, antibodies targeting the surface molecules of cancer cells, antibodies targeting growth factors or their receptors, inhibitors of metalloproteinases, metals, inhibitors of oncogenes, inhibitors of gene transcription or of RNA translation or protein expression, complexes of rare earth elements, and photo-chemotherapeutic agents.

In other embodiments, the chemotherapeutic agent is selected from the group consisting of paclitaxel (taxol), docetaxel, a vinca alkaloid such as navelbine, vinblastin, vincristin, vindesine or vinorelbine, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an immunomodulatory drug such as thalidomide, its R- and S-enantiomers and its derivatives, or revimid (CC-5013)), an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), uracil mustard, fludarabine, gemcitabine, capecitabine, mercaptopurine, cladribine, thioguanine, methotrexate, pentostatin, hydroxyurea, or folic acid, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, a proteasome inhibitor such as bortezomib, a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, an antagonist of the mitogen-activated protein kinase such as BAY-43-9006 or BAY-57-9006, a dual EGFR/IER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, a quinazoline derivative such as 4-[(3-chloro-4-fluorophenyl)amino]-6-{[-4-(N,N-dimethylamino)-1-oxo-2-but-1-en-1-yl]amino}-7-((S)-tetrahydrofuran-3-yloxy)-quinazoline or 4-[(3-chloro-4-fluoro-phenyl)amino]-6-{[4-(homomorpholin-4-yl)-1-oxo-2-bu- -ten-1-yl]amino}-7-[(S)-(tetrahydrofuran-3-yl)oxy]-quinazoline, or a pharmaceutically acceptable salt thereof, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, and an antibody targeting the surface molecules of cancer cells such as apolizumab or 1D09C3.

In some embodiments, the anti-cancer agent is an immune checkpoint inhibitor. In some embodiments, the immune checkpoint inhibitor is an inhibitor of CTLA4, such as an anti-CTLA4 antibody (e.g., ipilimumab (BMS), tremelimumab (AstraZeneca) and/or KAHR-102 (Kahr Medical)). In some embodiments, the immune checkpoint inhibitor is an inhibitor of PD-1, such as an anti-PD-1 antibody (e.g., nivolumab (BMS), pembrolizumab/lambrolizumab (Merck), pidilizumab (Curetech), AMP-224 (GSK), AMP-514 (AstraZeneca), STI-A1110 (Sorrento) and/or TSR-042 (Tesaro). In some embodiments, the immune checkpoint inhibitor is an inhibitor of PD-L1 and/or PD-L2, such as an anti-PD-L1 and/or an anti-PD-L2 antibody (e.g., RG-7446 (Roche), BMS-936559 (BMS), MEDI-4736 (AstraZeneca), MSB-0020718C (Merck), AUR-012 (Pierre Fabre Med), STI-A1010 (Sorrento)).

In some embodiments, the composition comprises a nucleic acid encoding an AMHR2 polypeptide described herein, such as a DNA molecule encoding an AMHR2 polypeptide. In some embodiments the composition comprises an expression vector comprising an open reading frame encoding an AMHR2 polypeptide.

When taken up by a cell (e.g., muscle cell, an antigen-presenting cell (APC) such as a dendritic cell, macrophage, etc.), a DNA molecule can be present in the cell as an extrachromosomal molecule and/or can integrate into the chromosome. DNA can be introduced into cells in the form of a plasmid which can remain as separate genetic material. Alternatively, linear DNAs that can integrate into the chromosome can be introduced into the cell. Optionally, when introducing DNA into a cell, reagents which promote DNA integration into chromosomes can be added.

Therapeutic Methods

In certain aspects, provided herein are methods for treating or preventing ovarian cancer and/or for inducing an immune response against an ovarian cancer tumor or AMHR2. In certain embodiments, the method comprises administering to a subject a pharmaceutical composition described herein. In some embodiments, the ovarian cancer tumor is a primary tumor. In some embodiments, the ovarian cancer tumor is a metastatic tumor. In some embodiments, the ovarian cancer tumor is an epithelial ovarian cancer (EOC) tumor. In some embodiments, the ovarian cancer tumor expresses AMHR2.

The methods described herein can be used to treat any subject in need thereof. As used herein, a "subject in need thereof" includes any subject who has ovarian cancer, who has had ovarian cancer and/or who is predisposed to ovarian cancer. For example, in some embodiments, the subject has an ovarian cancer tumor (e.g., an ovarian cancer tumor expressing AMHR2). In some embodiments, the subject has undergone surgery to remove at least part of an ovarian cancer tumor. In some embodiments, the subject is predisposed to ovarian cancer due to having a BRCA1 or BRCA2 mutation in her genome that predisposes the subject to ovarian cancer. In some embodiments, the subject has a family history of ovarian cancer.

The pharmaceutical compositions disclosed herein may be delivered by any suitable route of administration, including orally and parenterally. In certain embodiments the pharmaceutical compositions are delivered generally (e.g., via oral or parenteral administration).

The dosage of the subject agent may be determined by reference to the plasma concentrations of the agent. For example, the maximum plasma concentration (Cmax) and the area under the plasma concentration-time curve from time 0 to infinity (AUC (0-4)) may be used. Dosages include those that produce the above values for Cmax and AUC (0-4) and other dosages resulting in larger or smaller values for those parameters.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents employed in the pharmaceutical composition at levels lower than that required in order to achieve the desired therapeutic effect and gradually increase the dosage until the desired effect is achieved.

In general, a suitable daily dose of an agent described herein will be that amount of the agent which is the lowest dose effective to produce a therapeutic effect. Such an effective dose will generally depend upon the factors described above.

In one aspect, provided herein is a method of eliciting in a subject an immune response to a cell that expresses AMHR2 (e.g., an ovarian cancer tumor cell). The method comprises: administering to the subject a pharmaceutical composition described herein, wherein the pharmaceutically acceptable composition, when administered to the subject, elicits an immune response to the cell that expresses AMHR2.

Generally, the immune response can include a humoral immune response, a cell-mediated immune response, or both.

A humoral response can be determined by a standard immunoassay for antibody levels in a serum sample from the subject receiving the pharmaceutical composition. A cellular immune response is a response that involves T cells and can be determined in vitro or in vivo. For example, a general cellular immune response can be determined as the T cell proliferative activity in cells (e.g., peripheral blood leukocytes (PBLs)) sampled from the subject at a suitable time following the administering of a pharmaceutically acceptable composition. Following incubation of e.g., PBMCs with a stimulator for an appropriate period, [$^3$H]thymidine incorporation can be determined. The subset of T cells that is proliferating can be determined using flow cytometry.

In certain aspects, the methods provided herein include administering to both human and non-human mammals. Veterinary applications also are contemplated. In some embodiments, the subject can be any living female organism in which an immune response can be elicited. Examples of subjects include, without limitation, humans, livestock, dogs, cats, mice, rats, and transgenic species thereof.

In certain embodiments, the subject has a history of ovarian cancer and has been administered another mode of therapy. The other therapy may have included e.g., surgical resection, radiotherapy, chemotherapy, and other modes of immunotherapy whereby as a result of the other therapy, the subject presents no clinically measurable tumor. However, the subject can be one determined to be at risk for recurrence or progression of the cancer, either near the original tumor site, or by metastases. Such subjects can be further categorized as high-risk and low-risk subjects. The subdivision can be made on the basis of features observed before or after the initial treatment. These features are known in the clinical arts, and are suitably defined for each different cancer. Features typical of high risk subgroups are those in which the tumor has invaded neighboring tissues, or which show involvement of lymph nodes. Thus, for example, a pharmaceutical composition described herein can be administered to the subject to elicit an anti-cancer response primarily as a prophylactic measure against recurrence.

In some embodiments, the pharmaceutical composition can be administered at any time that is appropriate. For example, the administering can be conducted before or during traditional therapy of a subject having an ovarian cancer tumor, and continued after the tumor becomes clinically undetectable. The administering also can be continued in a subject showing signs of recurrence.

In some embodiments, the pharmaceutical composition can be administered in a therapeutically or a prophylactically effective amount. Administering the pharmaceutical composition to the subject can be carried out using known procedures, and at dosages and for periods of time sufficient to achieve a desired effect.

In some embodiments, the pharmaceutical composition can be administered to the subject at any suitable site, for example a site that is distal to or proximal to a primary tumor. The route of administering can be parenteral, intramuscular, subcutaneous, intradermal, intraperitoneal, intranasal, intravenous (including via an indwelling catheter), via an afferent lymph vessel, or by any other route suitable in view of the neoplastic disease being treated and the subject's condition. Preferably, the dose will be administered in an amount and for a period of time effective in bringing about a desired response, be it eliciting the immune response or the prophylactic or therapeutic treatment of the neoplastic disease and/or symptoms associated therewith.

The pharmaceutically acceptable composition can be given subsequent to, preceding, or contemporaneously with other therapies including therapies that also elicit an immune response in the subject. For example, the subject may previously or concurrently be treated by chemotherapy, radiation therapy, and other forms of immunotherapy, such other therapies preferably provided in such a way so as not to interfere with the immunogenicity of the compositions described herein.

Administering can be properly timed by the care giver (e.g., physician, veterinarian), and can depend on the clinical condition of the subject, the objectives of administering, and/or other therapies also being contemplated or administered. In some embodiments, an initial dose can be administered, and the subject monitored for an immunological and/or clinical response. Suitable means of immunological monitoring include using patient's peripheral blood lymphocyte (PBL) as responders and neoplastic cells as stimulators. An immunological reaction also can be determined by a delayed inflammatory response at the site of administering. One or more doses subsequent to the initial dose can be given as appropriate, typically on a monthly, semimonthly, or preferably a weekly basis, until the desired effect is achieved. Thereafter, additional booster or maintenance doses can be given as required, particularly when the immunological or clinical benefit appears to subside.

Cell Therapy

In certain aspects, an AMHR2 polypeptide described herein, or a nucleic acid encoding such an AMHR2 polypeptide, can be used in compositions and methods for providing AMHR2-primed, antigen-presenting cells, and/or AMHR2-specific lymphocytes generated with these antigen-presenting cells. In some embodiments, such antigen-presenting cells and/or lymphocytes are used in the treatment or prevention of ovarian cancer.

In some aspects, provided herein are methods for making AMHR2-primed, antigen-presenting cells by contacting antigen-presenting cells with an AMHR2 polypeptide described herein, or nucleic acids encoding the at least one AMHR2 polypeptide, in vitro under a condition sufficient for the at least one AMHR2 polypeptide to be presented by the antigen-presenting cells.

In some embodiments, the AMHR2 polypeptide, or nucleic acid encoding the AMHR2 polypeptide, can be contacted with a homogenous, substantially homogenous, or heterogeneous composition comprising antigen-presenting cells. For example, the composition can include but is not limited to whole blood, fresh blood, or fractions thereof such as, but not limited to, peripheral blood mononuclear cells, buffy coat fractions of whole blood, packed red cells, irradiated blood, dendritic cells, monocytes, macrophages, neutrophils, lymphocytes, natural killer cells, and natural killer T cells. If, optionally, precursors of antigen-presenting cells are used, the precursors can be cultured under suitable culture conditions sufficient to differentiate the precursors into antigen-presenting cells. In some embodiments, the antigen-presenting cells (or precursors thereof) are selected from monocytes, macrophages, cells of myeloid lineage, B cells, dendritic cells, or Langerhans cells.

The amount of the AMHR2 polypeptide, or nucleic acid encoding the AMHR2 polypeptide, to be placed in contact with antigen-presenting cells can be determined by one of ordinary skill in the art by routine experimentation. Generally, antigen-presenting cells are contacted with the AMHR2 polypeptide, or nucleic acid encoding the AMHR2 polypeptide, for a period of time sufficient for cells to present the processed forms of the antigens for the modulation of T cells. In one embodiment, antigen-presenting cells are incubated in the presence of the AMHR2 polypeptide, or nucleic acid encoding the AMHR2 polypeptide, for less than about a week, illustratively, for about 1 minute to about 48 hours, about 2 minutes to about 36 hours, about 3 minutes to about 24 hours, about 4 minutes to about 12 hours, about 6 minutes to about 8 hours, about 8 minutes to about 6 hours, about 10 minutes to about 5 hours, about 15 minutes to about 4 hours, about 20 minutes to about 3 hours, about 30 minutes to about 2 hours, and about 40 minutes to about 1 hour. The time and amount of the AMHR2 polypeptide, or nucleic acid encoding the AMHR2 polypeptide, necessary for the antigen presenting cells to process and present the antigens can be determined, for example using pulse-chase methods wherein contact is followed by a washout period and exposure to a read-out system e.g., antigen reactive T cells.

In certain embodiments, any appropriate method for delivery of antigens to the endogenous processing pathway of the antigen-presenting cells can be used. Such methods include but are not limited to, methods involving pH-sensitive liposomes, coupling of antigens to adjuvants, apoptotic cell delivery, pulsing cells onto dendritic cells, delivering recombinant chimeric virus-like particles (VLPs) comprising antigen to the MHC class I processing pathway of a dendritic cell line.

In one embodiment, solubilized AMHR2 polypeptide is incubated with antigen-presenting cells. In some embodiments, the AMHR2 polypeptide can be coupled to a cytolysin to enhance the transfer of the antigens into the cytosol of an antigen-presenting cell for delivery to the MHC class I pathway. Exemplary cytolysins include saponin compounds such as saponin-containing Immune Stimulating Complexes (ISCOM5), pore-forming toxins (e.g., an alpha-toxin), and natural cytolysins of gram-positive bacteria such as listeriolysin O (LLO), streptolysin O (SLO), and perfringolysin O (PFO).

In some embodiments, antigen-presenting cells, such as dendritic cells and macrophage, can be isolated according to methods known in the art and transfected with polynucleotides by methods known in the art for introducing a nucleic acid encoding the AMHR2 polypeptide into the antigen-presenting cell. Transfection reagents and methods are known in the art and commercially available. For example, RNA encoding AMHR2 polypeptide can be provided in a suitable medium and combined with a lipid (e.g., a cationic lipid) prior to contact with antigen-presenting cells. Non-limiting examples of such lipids include LIPOFECTIN™ and LIPOFECTAMINE™. The resulting polynucleotide-lipid complex can then be contacted with antigen-presenting cells. Alternatively, the polynucleotide can be introduced into antigen-presenting cells using techniques such as electroporation or calcium phosphate transfection. The polynucleotide-loaded antigen-presenting cells can then be used to stimulate T lymphocyte (e.g., cytotoxic T lymphocyte) proliferation in vivo or ex vivo. In one embodiment, the ex vivo expanded T lymphocyte is administered to a subject in a method of adoptive immunotherapy.

In certain aspects, provided herein is a composition comprising antigen-presenting cells that have been contacted in vitro with an AMHR2 polypeptide, or a nucleic acid encoding an AMHR2 polypeptide, under a condition sufficient for an AMHR2 epitope to be presented by the antigen-presenting cells.

In some aspects, provided herein is a method for preparing lymphocytes specific for AMHR2. The method comprises contacting lymphocytes with the antigen-presenting cells described above under conditions sufficient to produce an AMHR2-specific lymphocyte capable of eliciting an immune response against a cell that expresses AMHR2. Thus, the antigen-presenting cells also can be used to provide lymphocytes, including T lymphocytes and B lymphocytes, for eliciting an immune response against cell that expresses AMHR2.

In some embodiments, a preparation of T lymphocytes is contacted with the antigen-presenting cells described above for a period of time, (e.g., at least about 24 hours) to priming the T lymphocytes to an AMHR2 epitope presented by the antigen-presenting cells.

In some embodiments, a population of antigen-presenting cells can be co-cultured with a heterogeneous population of peripheral blood T lymphocytes together with an AMHR2 polypeptide, or a nucleic acid encoding an AMHR2 polypeptide. The cells can be co-cultured for a period of time and under conditions sufficient for AMHR2 epitopes included in the AMHR2 polypeptides to be presented by the antigen-presenting cells and the antigen-presenting cells to prime a population of T lymphocytes to respond to cells that express a AMHR2. In certain embodiments, provided herein are T lymphocytes and B lymphocytes that are primed to respond to cells that express a AMHR2.

T lymphocytes can be obtained from any suitable source such as peripheral blood, spleen, and lymph nodes. The T lymphocytes can be used as crude preparations or as partially purified or substantially purified preparations, which can be obtained by standard techniques including, but not limited to, methods involving immunomagnetic or flow cytometry techniques using antibodies.

In certain aspects, provided herein is a composition (e.g. a pharmaceutical composition) comprising the antigen-presenting cells or the lymphocytes described above, and a pharmaceutically acceptable carrier and/or diluent. In some embodiments, the composition further comprises an adjuvant as described above.

In certain aspects, provided herein is a method for eliciting an immune response to the cell that expresses AMHR2, the method comprising administering to the subject the antigen-presenting cells or the lymphocytes described above in effective amounts sufficient to elicit the immune response. In some embodiments, provided herein is a method for treatment or prophylaxis of ovarian cancer, the method comprising administering to the subject an effective amount of the antigen-presenting cells or the lymphocytes described above. In one embodiment, the antigen-presenting cells or the lymphocytes are administered systemically, preferably by injection. Alternately, one can administer locally rather than systemically, for example, via injection directly into tissue (e.g., into tissue proximal to an ovarian cancer tumor, such as into ovarian tissue), preferably in a depot or sustained release formulation.

In certain embodiments, the antigen-primed antigen-presenting cells described herein and the antigen-specific T lymphocytes generated with these antigen-presenting cells can be used as active compounds in immunomodulating compositions for prophylactic or therapeutic treatment of ovarian cancer. In some embodiments, the AMHR2-primed antigen-presenting cells described herein can be used for generating CD8$^+$ T lymphocytes, CD4$^+$ T lymphocytes, and/or B lymphocytes for adoptive transfer to the subject. Thus, for example, AMHR2-specific lymphocyte can be adoptively transferred for therapeutic purposes in subjects afflicted with ovarian cancer.

In certain embodiments, the antigen-presenting cells and/or lymphocytes described herein can be administered to a subject, either by themselves or in combination, for eliciting an immune response, particularly for eliciting an immune response to cells that express a AMHR2. In some embodiments, the antigen-presenting cells and/or lymphocytes can be derived from the subject (i.e., autologous cells) or from a different subject that is MHC matched or mismatched with the subject (e.g., allogeneic).

Single or multiple administrations of the antigen-presenting cells and lymphocytes can be carried out with cell numbers and treatment being selected by the care provider (e.g., physician). In some embodiments, the antigen-presenting cells and/or lymphocytes are administered in a pharmaceutically acceptable carrier. Suitable carriers can be the growth medium in which the cells were grown, or any suitable buffering medium such as phosphate buffered saline. The cells can be administered alone or as an adjunct therapy in conjunction with other therapeutics.

EXEMPLIFICATION

Figure 10:
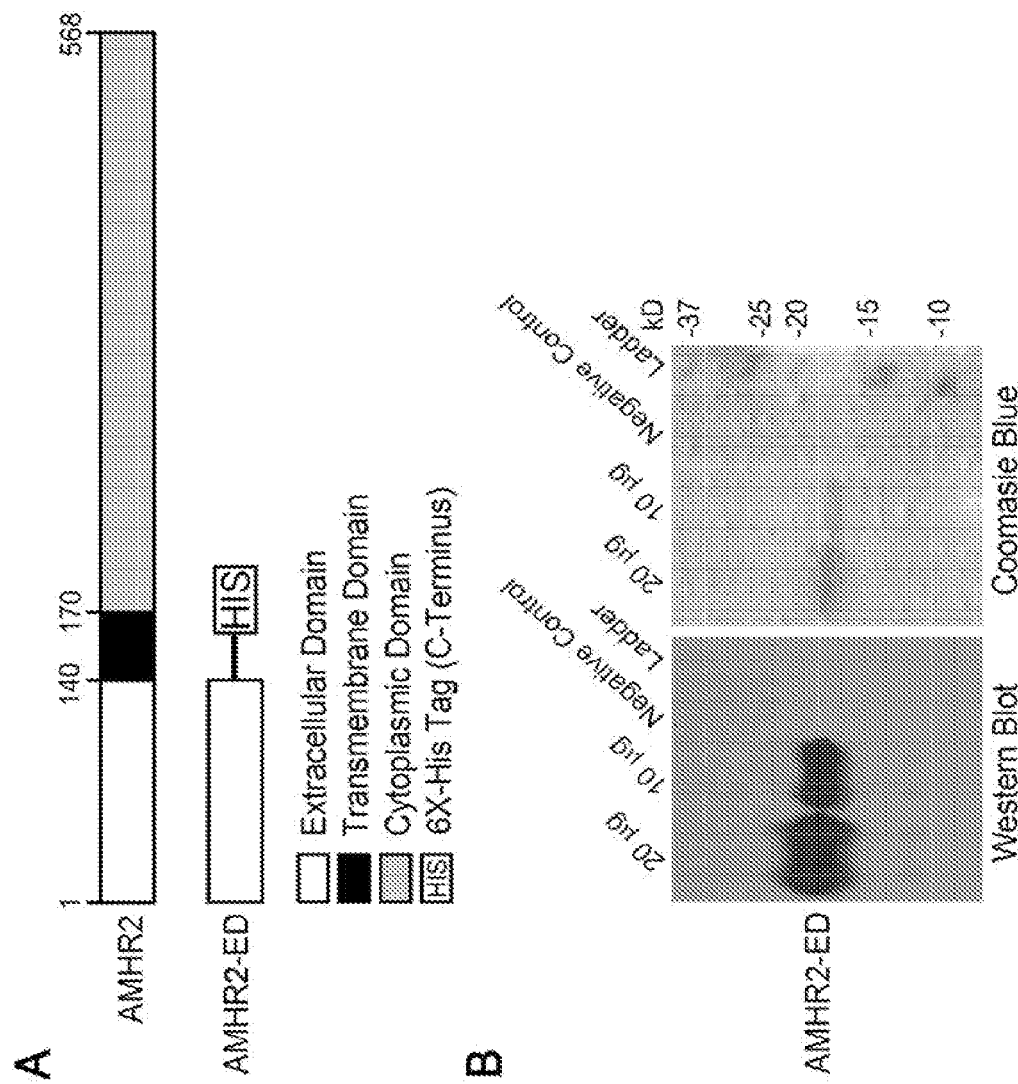
FIG. 10 has eight panels. Panel (A) is a schematic representation of full-length mouse AMHR2 (upper) as well as the 140 amino acid AMHR2-ED HIS-tagged truncated variant selected for production as a recombinant immunogen. Panel (B) shows an anti-His Western blot of SDS-PAGE gel showing expression of Ni-NTA affinity purified AMHR2-ED at two loaded doses (left) and Coomasie Blue stain of same (right). Panel (C) shows one month after AMHR2-ED vaccination of eight week old female C57BL/6 mice; ELISPOT analysis showed elevated splenocyte frequencies of antigen-specific T cells producing IFNγ and IL-17 but not IL-5. Panel (D) shows IFNγ and panel (E) shows IL-17 proinflammatory response to AMHR2-ED was due predominantly to responding CD4+ T cells but also incorporated a noticeable response from CD8+ T cells. Panel (F) shows AMHR2-ED vaccination induced a substantial serum IgG antibody response against AMHR2-ED that was detectable at dilutions up to 1/50,000 and panel (G) shows predominantly involved the IgG1 and IgG2b isotypes. Panel (H) shows that the immunogenicity of AMHR2-ED was not confined to C57BL/6 mice since female mice representing three other divergent H-2 haplotypes showed high antigen-specific frequencies of IFNγ-producing T cells. In all cases, error bars indicate ±SD.
Figure 10:
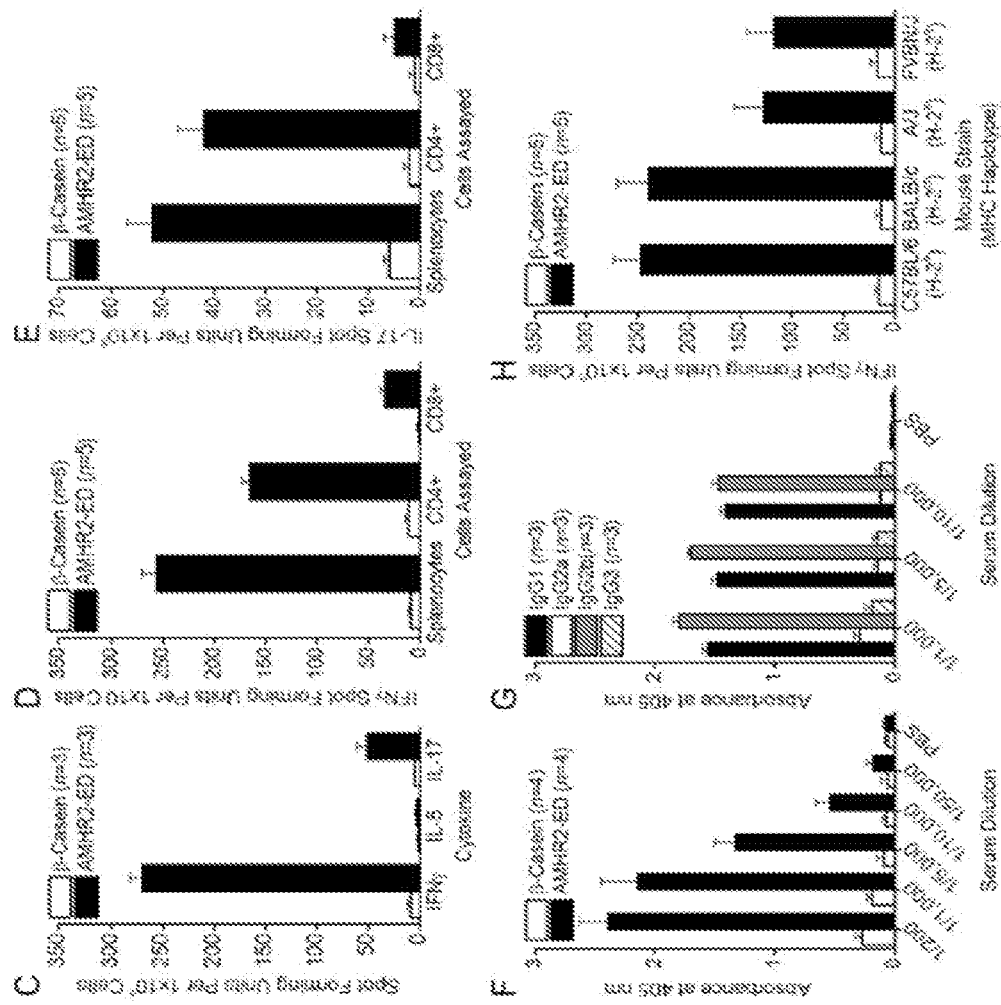

Experimental Procedures
Generation of Recombinant Mouse AMHR2 Polypeptides.
Total mRNA was extracted from ovaries of 8 week old female C57BL/6 mice. Primer pairs designed to amplify the AMHR2 sequence 1-140 or 170-568 were used to generate cDNA encoding either the entire 140 amino acid extracellular domain or the entire 399 amino acid cytoplasmic domain of mouse AMHR2 by RT-PCR. To optimize protein folding and enhance overall yield, substitutions for native codon sequences were made (Dapcel, Cleveland, OH), and the optimized cDNA was inserted into the NdeI-Bam HI site of pET-3a (Novagen, Darmstadt, Germany) thereby providing a C-terminal 6×His-tagged recombinant protein (FIGS. 1A and 10A). E. coli were transformed with plasmids containing these inserts. High level expression colonies were selected following induction with isopropylthiogalactopyronidase (IPTG; Amresco, Solon OH) and were sequenced to confirm proper orientation and alignment. The 6×His-tagged AMHR2 polypeptides were purified under denaturing conditions using nickel-nitrilo triacetic acid (Ni-NTA) affinity chromatography (Qiagen Sciences, Germantown, MD). The purified AMHR2 polypeptides were electrophoresed on denaturing SDS-PAGE gels (Bio-Rad, Hercules, CA) and blotted onto immunblot PVDF membrane (Bio-Rad). Immune detection of AMHR2 polypeptide was performed using the enhanced chemiluminescence system (Amersham Biosciences, Piscataway, NJ) with HRP-conjugated His antibody (Qiagen). Prior to use, the 6×His-tagged AMHR2 polypeptides were purified by reverse phase HPLC to yield endotoxin-free protein. Levels of endotoxin were <0.05 endotoxin units (<5 pg) per mg of recombinant protein.

Mice and Immunization.
Female C57BL/6 mice served as recipients of ID8 tumors. Mice were obtained commercially (Jackson Laboratory, Bar Harbor, ME) at six weeks of age and immunized at 7-10 weeks of age by subcutaneous injection in the abdominal flanks with 100 μg of recombinant mouse AMHR2-CD or AMHR2-ED in 200 μl of an emulsion of equal volumes of water and complete Freund's adjuvant (CFA; Difco, Detroit, MI) containing 400 g of Mycobacteria tuberculosis. TgMlSIIR-TAg (DR26 line) transgenic mice were maintained by breeding male TgMlSIIR-TAg (H-2$^b$) mice to wild-type syngeneic C57BL/6 females (Jackson Laboratory). TgMlSIIR-TAg mice were immunized at 6-7 weeks of age with 100 μg of recombinant mouse AMHR2-CD or AMHR2-ED in CFA as described above. To determine fertility phenotypes, age-matched test and control vaccinated C57BL/6 female mice were mated with the same C57BL/6 males.

Tumor Inoculation and Measurement.
ID8 cells were cultured in 75 or 225 cm$^2$ tissue culture flasks (BD Biosciences, Franklin Lakes, NJ) in DMEM (Mediatech Cellgro, Manassas, VA) containing 4% fetal bovine serum (Thermo Scientific Hyclone, Logan, UT), 1% penicillin/streptomycin (Invitrogen, Carlsbad, CA), and insulin-transferrin-sodium selenite media supplement (Sigma-Aldrich, St. Louis, MO) until the cells became 70-80% confluent. Cells were harvested by trypsinization and washed twice with PBS. Female C57BL/6 mice were inoculated subcutaneously in the left dorsal flank with 5×10$^6$ ID8 cells. Growth of ID8 tumors was assessed regularly by using a Vernier caliper to measure length×width. Tumor growth endpoint was determined by a measurement in any direction of 17 mm.

In Vivo Imaging and Measurement of Autochthonous Ovarian Tumors.
Bilateral ovarian tumor growth in female transgenic mice was measured monthly by ultrasound using the Vevo 770 high-resolution in vivo micro-imaging system for small animals (VisualSonics, Toronto, Canada). Real-time imaging of the abdomen was performed using the RMV704 low frequency probe/scan head and aqueous conductive gel after removing hair from the abdominal region. Anesthesia for immobilization was administered using a nose cone with continuous flow of 1-2% vol/vol isoflurane during the image acquisition period lasting less than 30 minutes, and oxygen supply was continuously maintained. The probe/scan head was moved over the abdominal area very gently after applying aqueous conductive gel. Measurements and calculation of tumor area were performed using the Vevo software B-Mode measurement tool allowing for a 2-D assessment of ovarian tumor size in vivo with the polygon region of interest setting (VisualSonics). Measurement of solid tumor size by B-mode sonography has been shown to correlate well with histopathologic measurement.

RT-PCR.
Tissues were excised and stored frozen in RNA-Later (Life Technologies, Grand Island, NY). RNA was either extracted from each tissue by homogenization in TRIZOL reagent (Invitrogen), or purchased commercially (OriGene Technologies, Rockville, MD; and ILS Biotech, Chestertown, MD). cDNA was generated from bulk RNA using Superscript III (Invitrogen). Gene expression was quantified by qRT-PCR using SYBR Green PCR mix (Applied Biosystems, Carlsbad, CA) with gene-specific primers (Table 1). Relative gene expression was assessed by normalization of each test gene expression level to β-actin expression levels in each individual tissue. Gene expression was determined by conventional RT-PCR using AMHR2- and β-actin-specific primers (Table 1). After amplification through 30 cycles, PCR products were separated on agarose gels (2% in 1 TBE buffer) and visualized under ultraviolet light after staining with ethidium bromide. Transgene expression in offspring of TgMISIIR-TAg mice was determined by PCR amplification of a 773 bp fragment of SV40-TAg using primer pairs as previously described (Table 1). DNA for the entire 140 amino acid sequence of the extracellular domain of mouse AMHR2 was amplified by RT-PCR from mouse ovarian tissues using AMHR2-specific primer pairs (Table 1).

dient centrifugation. The partially purified TILs were treated with Fcγ γIII/II receptor antibody (BD Biosciences) in PBS containing 0.5% BSA and 0.05% sodium azide and double-stained with FITC-conjugated anti-mouse CD3 and either PE-conjugated anti-mouse CD4 or PE-conjugated anti-mouse CD8 (BD Biosciences). The CD3$^+$ T cell population was gated and analyzed for percentages of CD4+ and CD8$^+$ T cells. Data collected on 30,000 total events were analyzed using FlowJo software (BD Biosciences).

Passive Transfer of Tumor Immunity.

Ten days after immunization of female C57BL/6 mice with AMHR2 polypeptide or control immunogen (ovalbumin; Sigma-Aldrich), LNCs at 5×10$^6$ cells/ml were activated in vitro with 20 µg/ml of immunogen in the presence of IL-12 (10 ng/ml) and IL-18 (10 ng/ml; Peprotech, Rocky Hill, NJ) in 24-well flat-bottom Falcon plates (BD Biosciences) in a total volume of 2.0 ml/well in DMEM supple-

TABLE 1

Primer Pairs Used for Cloning, qRT-PCR, Detection of Transgene, and for Conventional RT-PCR

| Protein | Sequence (5'-3') | SEQ ID NO: |
|---|---|---|
| AMHR2-ED (mouse) | F: AGCCCGAACCGCCGCCGCACCTGTG<br>R: CCCCGGGGTAGCCTGCGGTTCCTGC | 31<br>2 |
| AMHR2-CD (mouse) | F: CTGAGCCGCTGTTCCGATTTGA<br>R: ATGTTGGGGCGCTTCCTCTCCT | 3<br>4 |
| AMHR2-CD (human) | F: CGGGCAGCTGCAAGGAAAAC<br>R: CCCCGGCTGGCAGTGATAAA | 5<br>6 |
| AMHR2-ED (mouse) | F: GCGGGGAAGCACAAAGACACT<br>R: CCGGCCATGGGTAAGATTCC | 7<br>8 |
| AMHR2-ED (human) | F: GGGGCTTTGGGCATTACTTCC<br>R: CCGGTCTTGGGTCAGGTTCC | 9<br>10 |
| AMHR2-CD | F: GGATCCAAGGCCTGCAGAGTGCAAGGTG<br>R: AAGCTTCTACTCATTTACATACACCTG | 11<br>12 |
| SV40-TAg | F: TGCATGGTGTACAACATTCC<br>R: TTGGGACTGTGAATCAATGCC | 13<br>14 |
| IFNγ | F: GGATATCTGGAGGAACTGGCAA<br>R: TGATGGCCTGATTGTCTTTCAA | 15<br>16 |
| TNFα | F: CGAGTGACAAGCCTGTAGCC<br>R: GTGGGTGAGGAGCACGTAGT | 17<br>18 |
| IL-1β | F: AAGGAGAACCAAGCAACGACAAAA<br>R: TGGGGAACTCTGCAGACTCAAACT | 19<br>20 |
| IL-2 | F: GCAGGCCACAGAATTGAAAG<br>R: TCCACCACAGTTGCTGACTC | 21<br>22 |
| CD4 | F: ACACACCTGTGCAAGAAGCA<br>R: GCTCTTGTTGGTTGGGAATC | 23<br>24 |
| CD8 | F: TTACATCTGGGCACCCTTG<br>R: TTGCCTTCCTGTCTGACTAGC | 25<br>26 |
| ß-Actin | F: GGTCATCACTATTGGCAACG<br>R: ACGGATGTCAACGTCACACT | 27<br>28 |
| AMHR2 | F: GTATCCGCTGCCTCTACAGC<br>R: CAGAAGTCAGTGCCACAGGA | 29<br>30 |

Flow Cytometry Analysis of Tumor Infiltrating Lymphocytes (TILs).

TILs were isolated from ID8 tumors by digestion of minced tumor for 30 minutes at 37° C. in HBSS containing 50 KU of DNase I (Sigma-Aldrich) and 0.2 mg/ml collagenase II (Life Technologies) followed by discontinuous gramented as described above. After 3 days of restimulation, 2×10$^7$ activated whole LNCs were injected intraperitoneally into sublethally γ-irradiated (5 Gy) naive female recipients. Alternatively, C57BL/6 female mice were immunized with either AMHR2 polypeptide or OVA, and four weeks later, three groups of cells were injected intraperitoneally into sublethally γ-irradiated (5 Gy) naive female recipients including 7.5×10⁷ whole splenocytes reactivated with immunogen, IL-12, and IL-18 as described above, 2×10⁷ similarly reactivated CD4⁺ T cells purified from whole splenocytes by magnetic bead separation, and 2×10⁷ non-reactivated B220+ B cells also purified from whole splenocytes by magnetic bead separation. In all cases, hosts were inoculated subcutaneously on the day after cell transfer with 5×10⁶ ID8 cells, and tumor growth was assessed regularly as described above. Purities of enriched cells were determined by flow cytometry analysis using CellQuest software (BD Biosciences) and were consistently found to be >90%.
Biostatistical Analysis.

Differences between mRNA expression levels and mean tumor weights were compared using the Student's t-test. Differences between tumor growth curves were compared by unweighted one-way ANOVA, and differences in mouse survival curves were compared using the logrank test.

Example 1: Generation of Recombinant Mouse AMHR2-CD

The longest hydrophilic domain of mouse AMHR2 consisting of the 170-568 sequence comprising the 399 amino acids of the entire cytoplasmic domain was expressed (FIG. 1A). The Ni-NTA affinity purified C-terminal 6×His-tagged protein migrated as a ~44 kD protein as determined by Coomassie blue staining of an SDS-PAGE gel (FIG. 1B), and by Western blot immunostaining using HRP-conjugated His-specific antibody (FIG. 1C).

Example 2: Immunogenicity of AMHR2-CD

Figure 2:
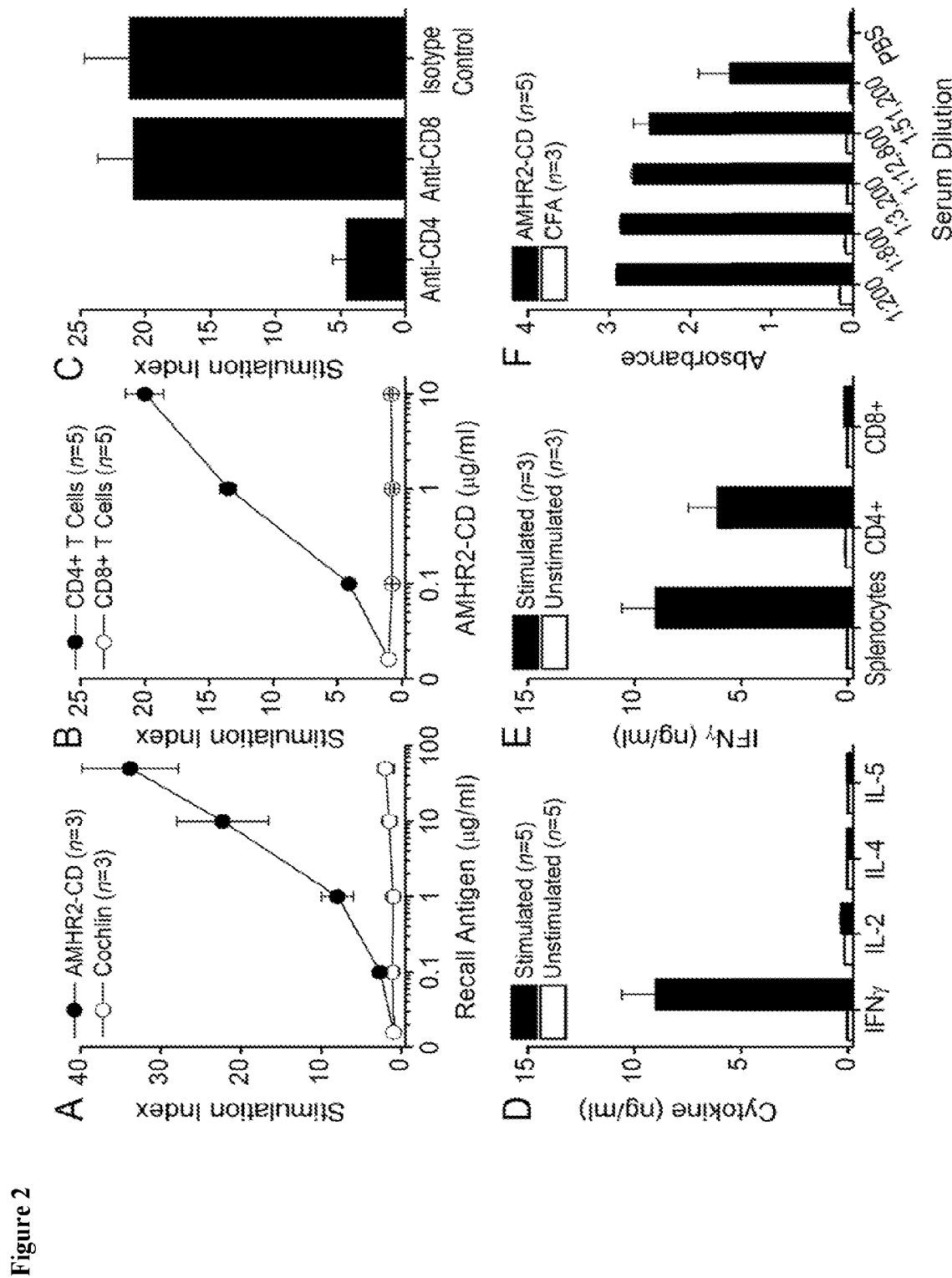
FIG. 2 has six panels and shows data resulting from the immunization of female C57BL/6 mice with AMHR2-CD in CFA, and LNC or splenocytes were cultured in vitro for assessment of proliferation and cytokine production. Panel (A) demonstrates that 10 day primed LNC showed marked antigen-specific recall proliferative responses to AMHR2-CD over several logs of antigen concentration. Panel (B) shows that a response to AMHR2-CD was elicited by CD4$^+$ T cells but not by CD8$^+$ T cells purified by magnetic bead separation. Panel (C) shows proliferative responses to AMHR2-CD were markedly inhibited in the presence of CD4 antibody but not in the presence of CD8 or isotype control antibodies. Panel (D) shows that four weeks after immunization, splenocytes were reactivated with immunogen and ELISA analysis of 72 hour culture supernatants showed that recall responses to AMHR2-CD involved a proinflammatory phenotype with elevated production of IFNγ and minimal production of IL-2, IL-4, and IL-5. Panel (E) shows splenocyte production of IFNγ was elicited from purified CD4+ T cells but not from purified CD8+ T cells. Panel (F) shows that two months after immunization, serum levels of AMHR2-CD-specific IgG were detectable even at titers over a 1:50,000 dilution. PBS was substituted for diluted sera in the PBS control. Error bars show ±SD.

Ten days after AMHR2-CD immunization of female C57BL/6 mice, LNC showed proliferation in a dose response manner to AMHR2-CD but not to recombinant human cochlin, a control protein generated and purified in a manner similar to AMHR2-CD (FIG. 2A). This antigen-specific proliferation by LNC was elicited from purified CD4⁺ T cells but not from purified CD8⁺ T cells (FIG. 2B) and was inhibited by treatment of cultures with CD4-specific but not CD8-specific antibodies (FIG. 2C). Four weeks after immunization, ELISA analysis of supernatants from immunogen-stimulated splenocytes showed a predominant proinflammatory response to AMHR2-CD with high production of IFNγ and with relatively low production of IL-2, IL-4, and IL-5 (FIG. 2D). Purification of T cell subsets from the whole splenocyte population showed that CD4+ but not CD8⁺ T cells produced the IFNγ in response to AMHR2-CD (FIG. 2E). Two months after immunization, serum levels of AMHR2-CD-specific IgG were detectable even at titers exceeding a 1:50,000 dilution (FIG. 2F).

Figure 3:
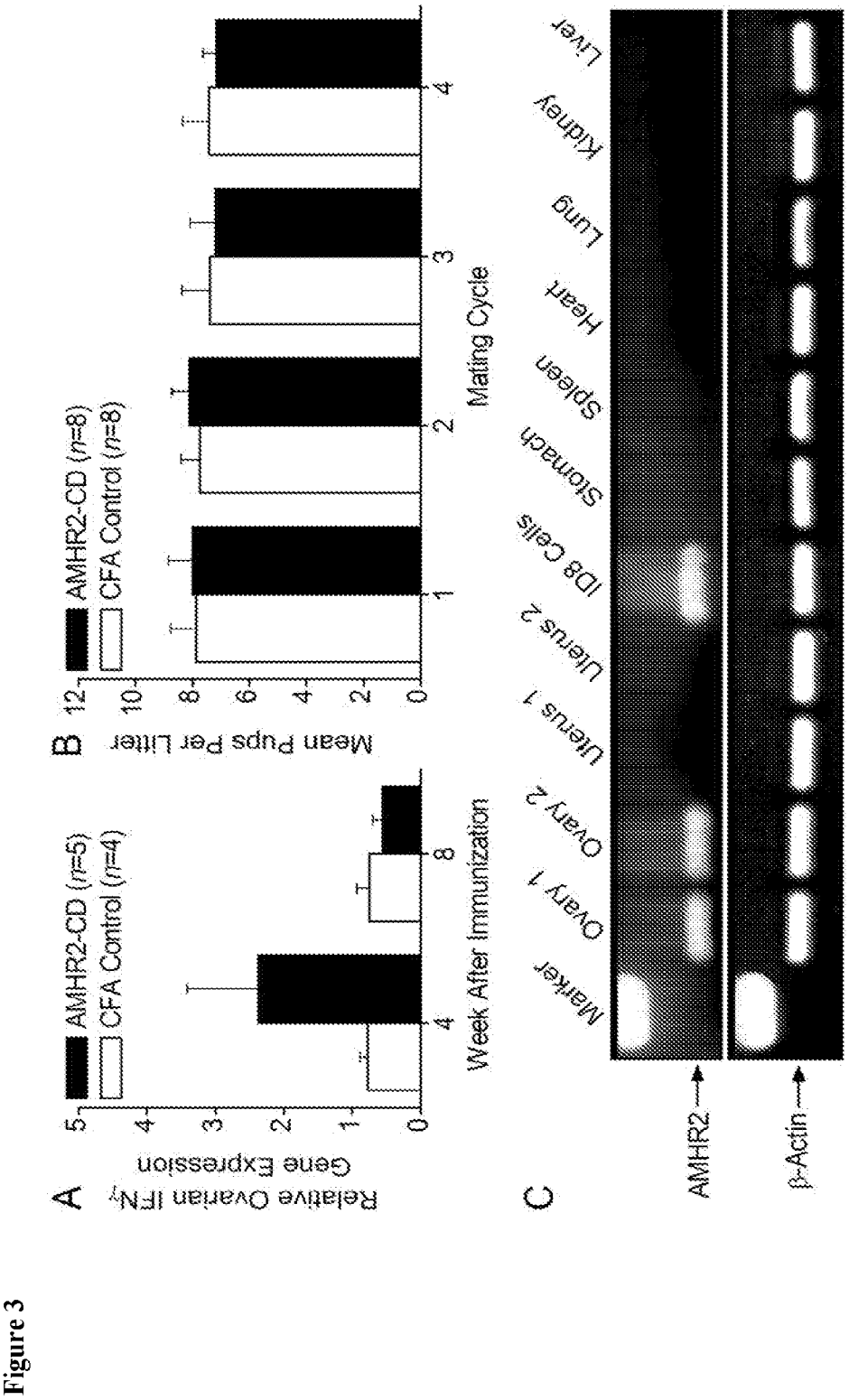
FIG. 3 has three panels and shows data related to benign transient ovarian inflammation following AMHR2-CD immunization. Panel (A) shows relative ovarian IFNγ gene expression was elevated 4 weeks after immunization with AMHR2-CD but not after immunization with CFA alone. At eight weeks after immunization, relative ovarian IFNγ gene expression was similar in both immunized groups of mice. Panel (B) shows the low level transient expression of IFNγ in ovaries of AMHR2-CD immunized mice was not associated with any detectable effect on ovarian function as determined by assessing fertility defined by pup production over four sequential mating cycles in female C57BL/6 mice immunized with AMHR2-CD and control mice immunized with CFA alone. Panel (C) shows that AMHR2 gene expression was confined to ovaries and ID8 ovarian tumor cells and was not detected in normal uterus, stomach, spleen, heart, lung, kidney, and liver. Error bars show ±SD.

Example 3: Benign Transient Ovarian Inflammation Following AMHR2-CD Immunization The potential of AMHR2-CD immunization to induce ovarian autoimmunity was next examined. Four and eight weeks after AMHR2-CD immunization of C57BL/6 female mice, ovarian IFNγ gene expression was measured by qRT-PCR. Relative ovarian IFNγ gene expression was modestly elevated 4 weeks after AMHR2-CD immunization but not after immunization with CFA alone (FIG. 3A). Eight weeks after immunization, relative ovarian IFNγ gene expression was similar in both immunized groups of mice. Most notably, the transiently elevated IFNγ gene expression observed in AMHR2-CD immunized mice at 4 weeks were only 3 fold higher than CFA control mice. No CD3⁺ T cell infiltrates were observed in ovaries by immunohistochemical analysis at 4, 8, and 12 weeks after AMHR2-CD immunization. The low transient expression of IFNγ in ovaries of AMHR2-CD immunized mice was not associated with any detectable effect on ovarian function as indicated by mouse fertility over four sequential mating cycles during which no significant differences (P>0.60) occurred in the number of pups generated per litter between AMHR2-CD and CFA immunized mice (FIG. 3C). AMHR2 gene expression was readily detected in the ovaries and ID8 ovarian tumor cells and was not detected at any appreciable levels in normal mouse uterus, stomach, spleen, heart, lung, kidney, and liver (FIG. 3C).

Example 4. Inhibition of Tumor Growth in Mice Immunized with AMHR2-CD

Figure 4:
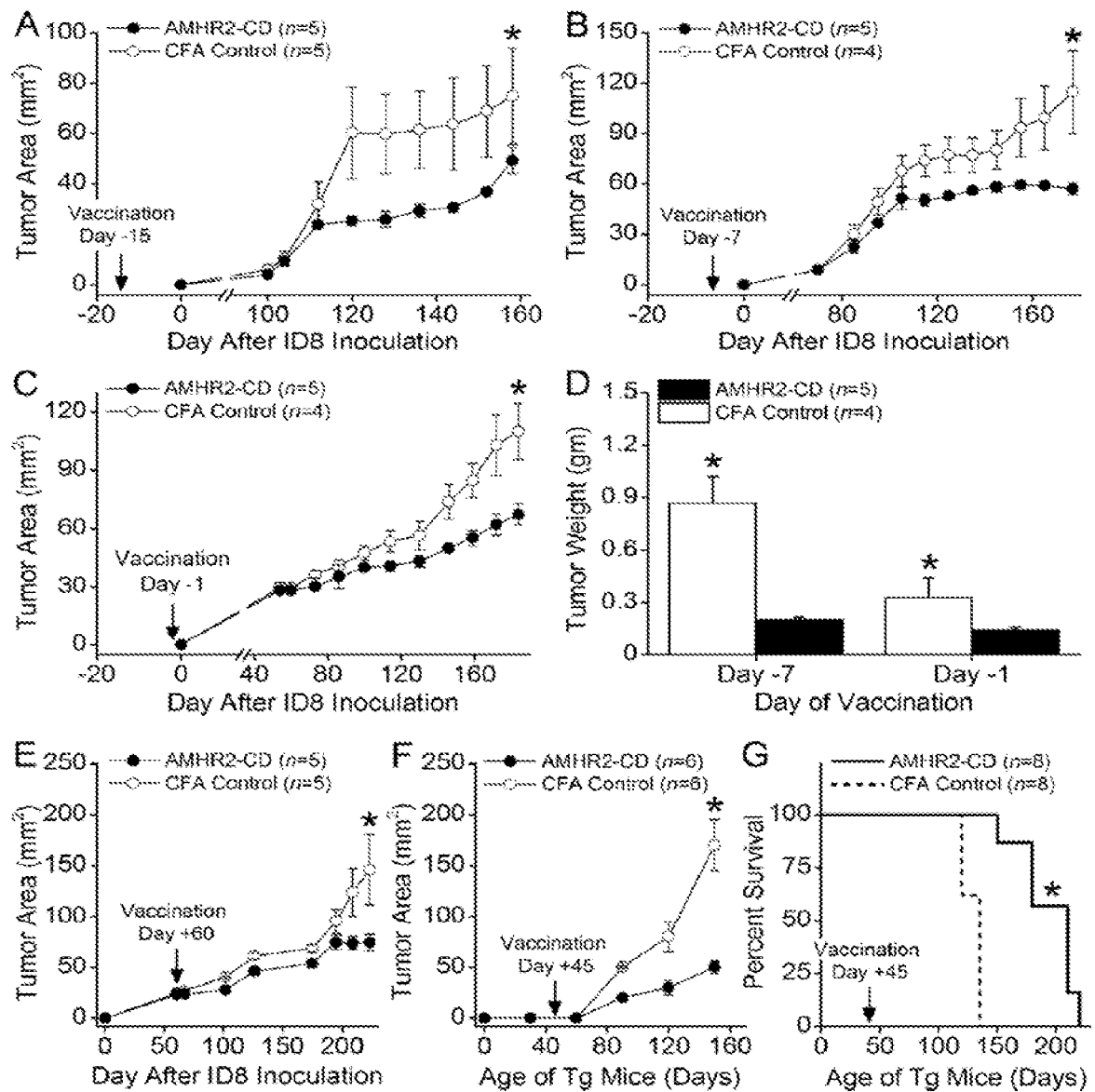
FIG. 4 has seven panels and shows data related to the inhibition of tumor growth in mice immunized with AMHR2-CD. As depicted in Figures (A), (B) and (C), respectively, ID8 tumor growth was inhibited in mice prophylactically vaccinated 5 days, 7 days or 1 day prior to inoculation of tumor cells. Panel (D) shows that AMHR2-CD vaccination resulted in a significantly decreased overall tumor load as measured by final tumor weight at termination of experiments in mice vaccinated 7 days and 1 day prior to ID8 inoculation. Panel (E) shows that therapeutic vaccination with AMHR2-CD 60 days after inoculation of ID8 tumors significantly inhibited the growth of established, palpable, growing ID8 tumors. Panel (F) shows that prophylactic vaccination of female TgMlSIIR-TAg transgenic mice at 6-7 weeks of age with AMHR2-CD resulted in a highly significant inhibition in growth of autochthonous EOC. Panel (G) shows that prophylactic AMHR2-CD vaccination of female TgMlSIIR-TAg transgenic mice at 6-7 weeks of age resulted in a highly significant 41.7% mean increased OS compared to control mice vaccinated with CFA alone. Asterisks indicate statistical significance. Error bars show ±SD.

Whether vaccination with AMHR2-CD would inhibit growth of transplantable ID8 tumors in C57BL/6 female mice was next determined. ID8 tumor growth was inhibited in mice prophylactically vaccinated 15 days (FIG. 4A; P<0.001), 7 days (FIG. 4V; P<0.001), or 1 day (FIG. 4C; P<0.05) prior to inoculation of ID8 ovarian tumor cells. In addition, AMHR2-CD vaccination resulted in a significantly decreased overall tumor load as measured by final ID8 tumor weight at termination of experiments in mice vaccinated 7 days (P<0.01) and 1 day (P<0.05) prior to ID8 inoculation (FIG. 4D). AMHR2-CD vaccination was also effective as therapy against EOC. Vaccination with AMHR2-CD 60 days after inoculation of ID8 tumors significantly inhibited the growth of established, palpable ID8 tumors (P<0.05; FIG. 4E). Vaccination with AMHR2-CD significantly inhibited the growth of autochthonous EOCs that develop spontaneously in TgMISIIR-TAg transgenic mice (P<0.0001; FIG. 4F). Moreover, this inhibition in tumor growth was accompanied by a highly significant increased overall survival (OS) when compared to CFA vaccinated control mice (P<0.0005; FIG. 4G). This enhanced lifespan in AMHR2-CD vaccinated mice (mean 191.25 days±22.95) compared to CFA vaccinated control mice (mean 135 days±13.89) represents a 41.7% increase in OS.

Figure 5:
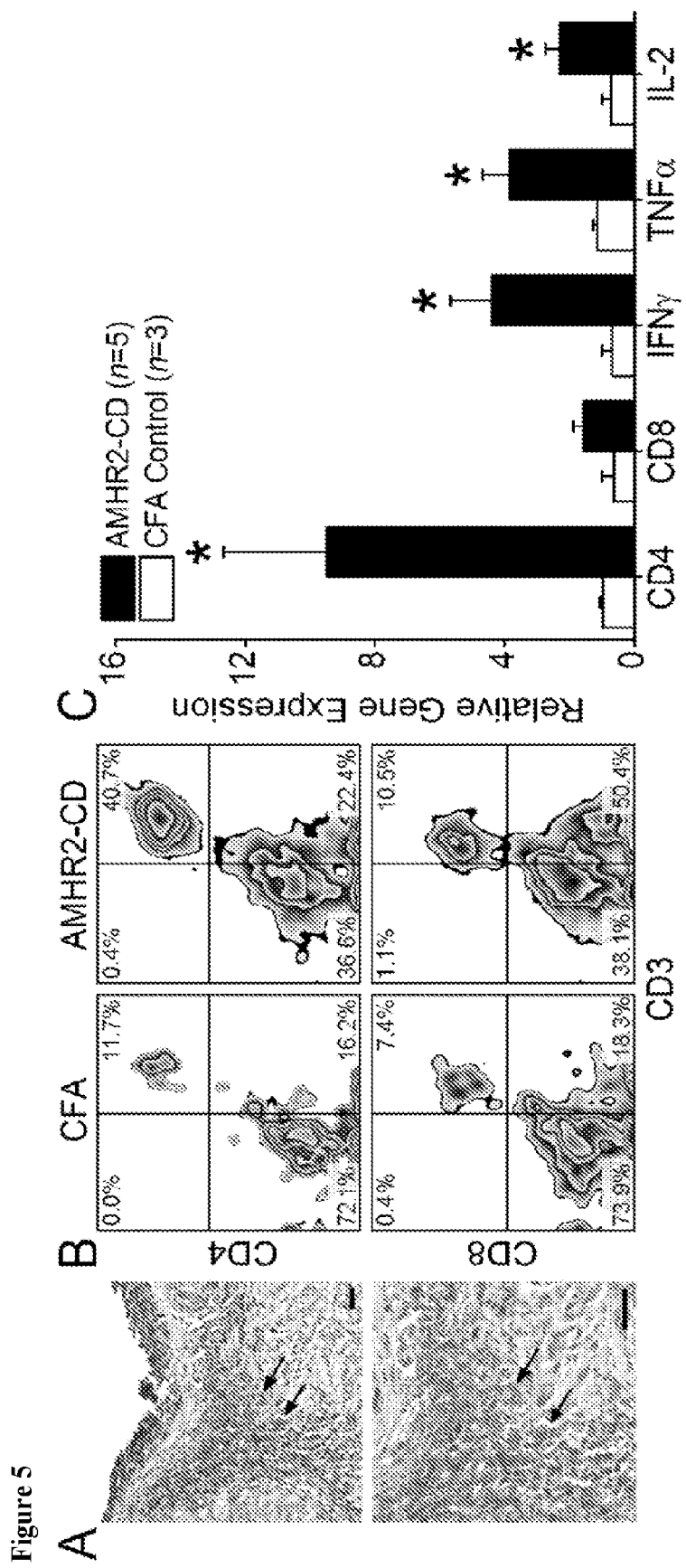
FIG. 5 has three panels and shows data related to tumor analysis. In panel (A), arrows indicate infiltration of CD3+ T cells in an ID8 tumor from AMHR2-CD vaccinated mice in lower resolution (top) and higher resolution (bottom) images. Inflammatory infiltrates of CD3+ T cells were never observed in control mice vaccinated with CFA alone. Panel (B) depicts a flow cytometry analysis of TILs gated on the CD3+ T cell population showed a pronounced increase in percentages of CD4+ T cells but not CD8+ T cells in tumor infiltrates from mice vaccinated with AMHR2-CD compared to control mice immunized with CFA alone. Data shown are representative of three experiments yielding similar results. Panel (C) shows that tumors from AMHR2-CD immunized mice consistently showed increased relative gene expression for CD4, IFNγ, TNFα, and IL-2 but not for CD8. Asterisks indicate statistical significance. Error bars show ±SD.

At the termination of experiments, tumors were analyzed for inflammatory infiltrates. Immunohistochemical analysis consistently showed extensive infiltration of CD3⁺ T cells in tumors from AMHR2-CD vaccinated mice (FIG. 5A). No infiltrates were observed in tumors from mice immunized with CFA alone. Flow cytometry analysis of TILs showed a pronounced increase of CD4⁺ T cells in tumors from mice vaccinated with AMHR2-CD compared to control mice immunized with CFA alone (40.7% vs. 11.7%; FIG. 5b). Substantial increases of CD8⁺ T cells in tumors did not occur in AMHR2-CD immunized mice compared to CFA immunized control mice (10.5% vs. 7.4%, respectively). Tumor RNA was next analyzed for gene expression of proinflammatory factors by qRT-PCR. When compared to tumors from CFA immunized control mice, tumors from AMHR2-CD immunized mice consistently showed significantly increased relative gene expression (P<0.05 in all cases) for CD4, IFNγ, TNFα, and IL-2 but not for CD8 (FIG. 5C). These data indicate the induction of a proinflammatory immune milieu within the ID8 tumor following immunization with AMHR2-CD.

Example 5: Passive Transfer of Tumor Immunity with CD4⁺ Cells

Figure 6:
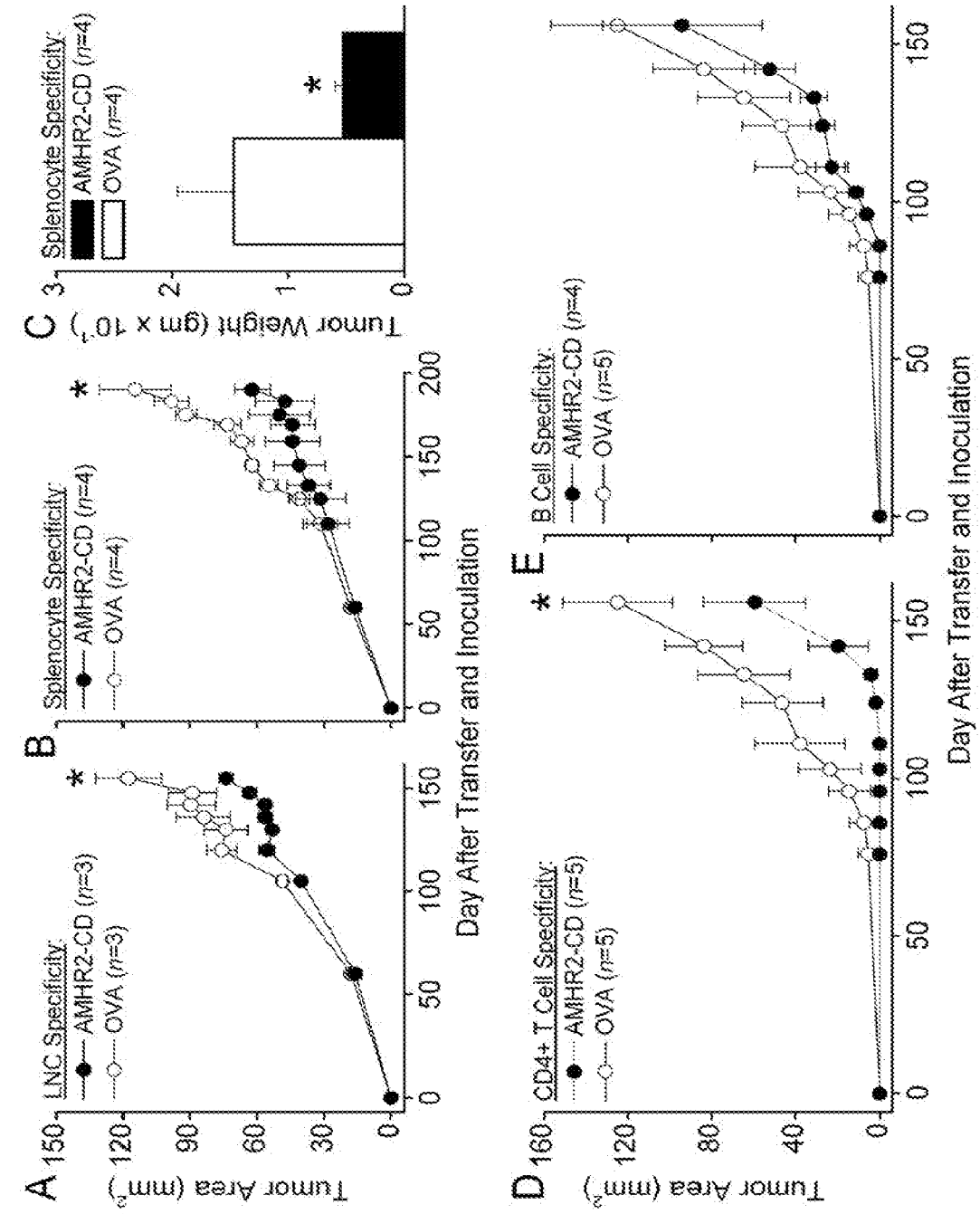
FIG. 6 has five panels and shows data related to the passive transfer of immune protection against tumor growth with CD4+ T cells. Recipient mice were inoculated with ID8 tumor cells on the day after cell transfer. Growth of ID8 tumors was inhibited in mice transferred with AMHR2-CD-specific LNCs (panel (A)) and splenocytes (panel (B)). Panel (C) shows that at 190 days after splenocyte transfer and inoculation, mean tumor weights were lower in recipients of AMHR2-CD-specific splenocytes compared to recipients of OVA-specific splenocytes. Panels (D) and (E) respectively show that transfer of purified AMHR2-CD-specific CD4+ T cells but not B220+ B cells inhibited ID8 tumor growth. Asterisks indicate statistical significance. Error bars show ±SE.

All recipient mice were inoculated with ID8 tumor cells on the day after cell transfer. Tumor growth was significantly inhibited in mice transferred with AMHR2-CD-specific LNCs (P=0.04; FIG. 6A) and splenocytes (P<0.01; FIG. 6B) when compared to mice receiving OVA-specific LNCs. At 190 days after transfer of primed splenocytes and tumor inoculation, mean tumor weights were significantly lower in recipients of AMHR2-CD-specific splenocytes compared to recipients of OVA-specific splenocytes (P<0.05; FIG. 6C). Transfer of AMHR2-CD-specific CD4$^+$ T cells purified from 4 week primed splenocytes resulted in significant inhibition of ID8 tumor growth compared to transfer of purified OVA-specific CD4$^+$ T cells (P<0.0004; FIG. 6D) whereas transfer of AMHR2-CD-primed B220$^+$ B cells purified from 4 week primed splenocytes did not significantly inhibit ID8 tumor growth compared to transfer of OVA-primed B220$^+$ B cells (P=0.07; FIG. 6D). Thus, AMHR2-CD-specific proinflammatory CD4$^+$ T cells are sufficient for transferring immune protection against the growth of EOC.

Example 6: Human AMHR2 Tissue Expression

Figure 7:
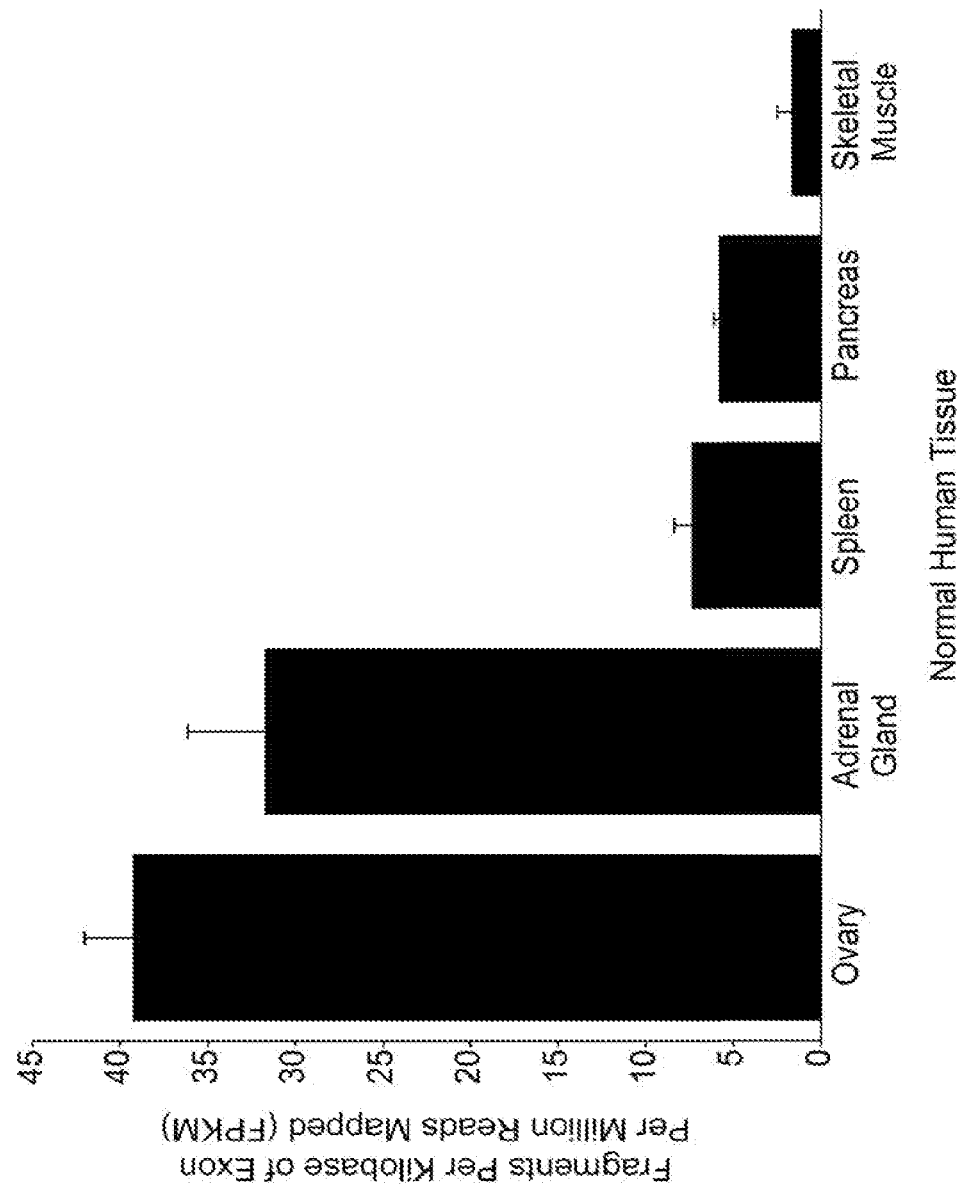
FIG. 7 shows AMHR2 gene expression in normal human tissues. Twenty-five other normal human tissues were also examined and showed no expression of AMHR2 above background levels.

The Human Protein Atlas database was examined to determine relative AMHR2 gene expression in thirty human tissues. As seen in FIG. 7, AMHR2 gene expression was observed to be above background in only five of the thirty tissues, with the highest expression observed in the ovary.

Figure 8:
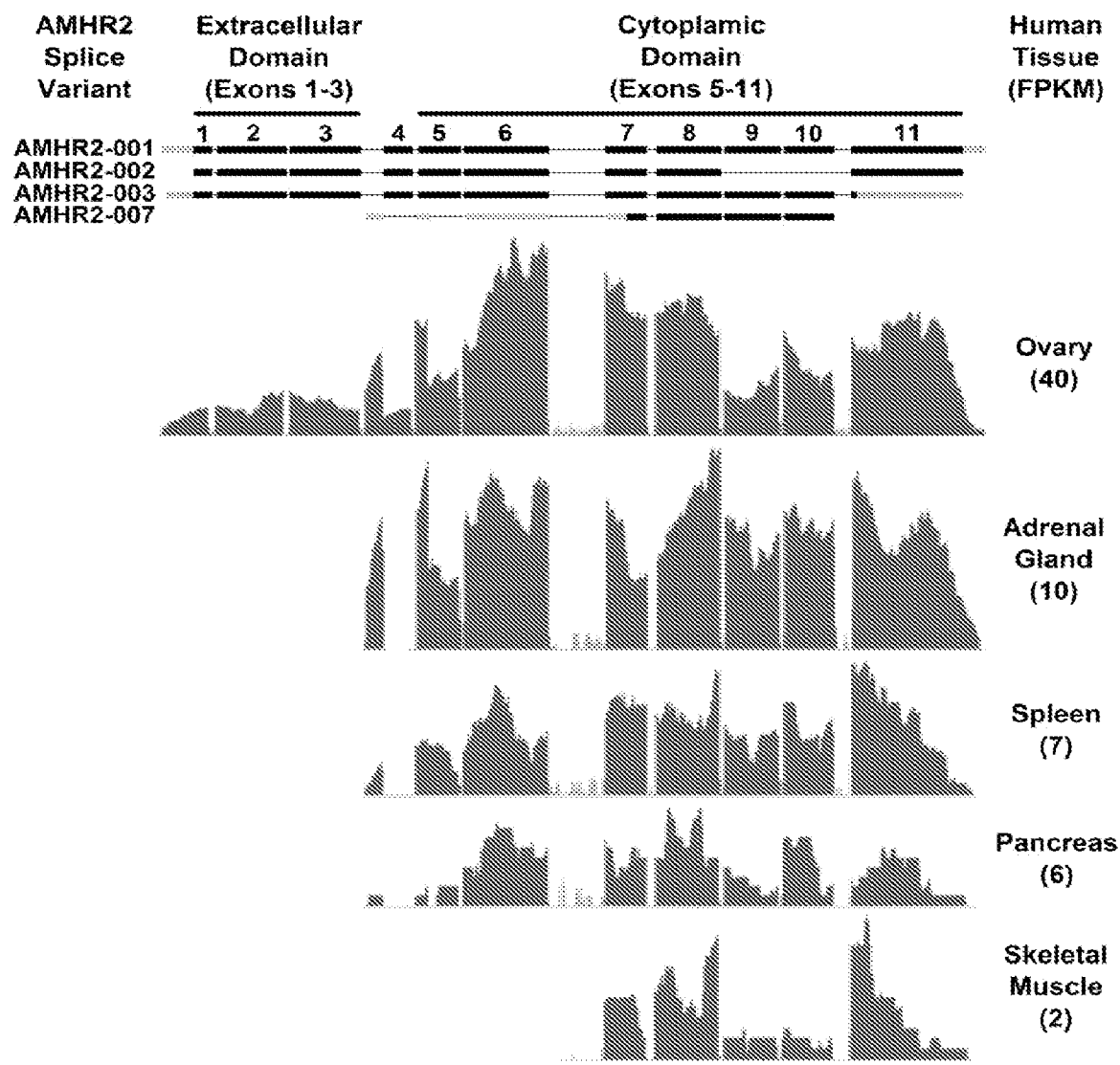
FIG. 8 has five panels and shows AMHR2 gene expression in human tissues. Panel (A) shows that the extracellular domain of AMHR2 is expressed in the ovary but not in other AMHR2-expressing tissues. Panel (B) shows that using primer pairs specific for AMHR2-CD and AMHR2-ED, qRT-PCR analysis of human tissues confirms findings from the Human Protein Atlas by indicating that AMHR2-ED is expressed exclusively in the human ovary and is not expressed in the human adrenal gland or pancreas. Panel (C) shows ovarian expression of human AMHR2 declines with age and this decline is particularly evident with respect to AMHR2-ED which is expressed at significantly lower levels in the postmenopausal ovary (mean age, 64 years) compared to the premenopausal ovary (mean age, 31 years). A similar significant decline in AMHR2-ED gene expression occurs in older mouse ovaries (9 months of age). Panel (D) shows the decline with age in ovarian expression of AMHR2 stands in contrast to the high level of gene expression of both AMHR2-CD and AMHR2-ED domains in human EOC. Panel (E) shows that this high AMHR2 gene expression in human EOC is accompanied by corresponding high levels of detectable AMHR2 protein determined by Western blot analysis on all 16 human EOC tumors examined using a polyclonal antibody specific for AMHR2-ED with 3-actin immunostaining serving as endogenous control. In all cases, error bars indicate ±SD, and asterisks indicate significance.
Figure 8:
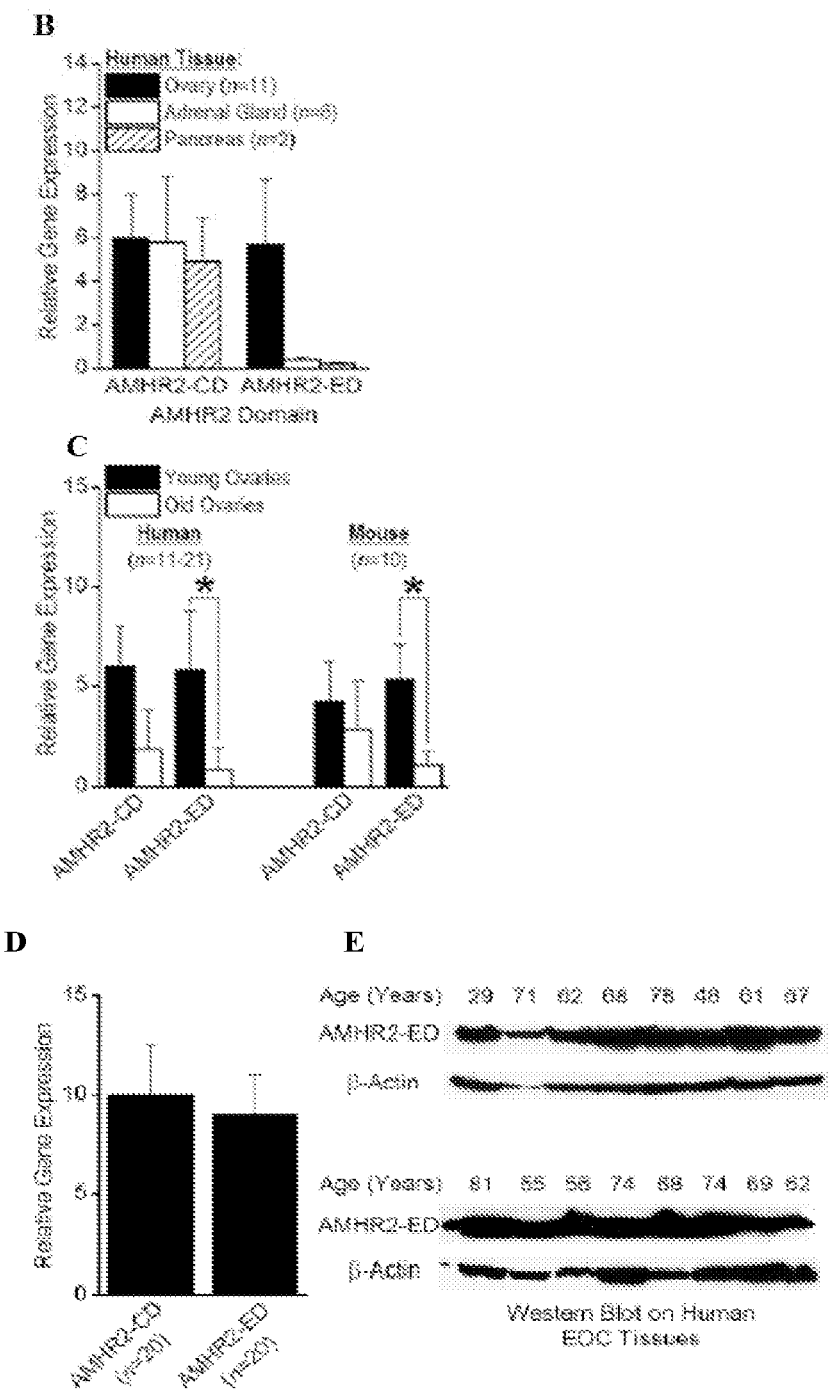

There are several known splice variants of AMHR2, with the various splice variants encoding different portions of AMHR2. The Human Protein Atlas was next examined to determine the level of expression of the different AMHR2 exons in the five tissues in which AMHR2 gene expression was observed. As seen in FIG. 8, expression of the exons encoding the extracellular domain of AMHR2 was confined exclusively to the ovary. Quantitative real-time RT-PCR (qRT-PCR) was used to show that expression of AMHR2-ED is confined to the normal human ovary and is not expressed in the human adrenal gland or pancreas (FIG. 8B). In addition, as seen in FIG. 8D, human postmenopausal ovaries (mean 64 years; range 52-95 years) and old mouse ovaries (nine months of age) have low levels of AMHR2-ED expression when compared respectively to human premenopausal ovaries (mean 31 years; range 27-45 years) and young mouse ovaries (6 weeks of age). Moreover, all human EOC tumors that were examined showed high level expression of both AMHR2-ED transcripts (as assessed by qRT-PCR; FIG. 8E) and protein (as assessed by Western blot analysis; FIG. 8F). Thus, expression levels of both domains decline with age in normal ovaries, reducing the probability of even transient oophoritis in vaccinating postmenopausal women with AMHR2 polypeptides.

Figure 9:
FIG. 9 has two panels and shows expression of the AMHR2 extracellular domain in human EOCs. Panel (A) shows that using primer pairs specific for AMHR2-ED, quantitative real-time RT-PCR analysis shows expression of AMHR2-ED in normal human ovaries (n=7) but not in normal human adrenal glands (n=3). Panel (B) shows a western blot analysis using a polyclonal antibody specific for the extracellular domain of AMHR2 shows detection of AMHR2-ED protein in all five human EOCs examined. The full-length protein was detected in only one of the five examined tumors suggesting that AMHR2 signaling may be altered in many EOCs due to possible deletions of regions of the cytoplasmic kinase domain. Antibody specific for 3-Actin was used as a control.

Real-time RT-PCR was used to confirm that the AMHR2 extracellular domain was expressed in normal human ovary, but not in the extracellular domain (FIG. 9A).

Whether the AMHR2 extracellular domain was expressed in EOCs was next tested. When five EOCs were tested by western blot using an antibody specific for the AMHR2 extracellular domain, extracellular domain expression was observed in all samples (FIG. 9B).

Example 7: Generation of Recombinant Mouse AMHR2-ED

The mouse AMHR2 extracellular domain made up of the N-terminal 140 amino acids of the AMHR2 protein was expressed (FIG. 10A). The Ni-NTA affinity purified C-terminal 6xHis-tagged protein migrated as a ~17 kD protein as determined by Coomassie blue staining of an SDS-PAGE gel and by Western blot immunostaining using HRP-conjugated His-specific antibody (FIG. 10B). One month after AMHR2-ED vaccination of young 6 week old C57BL/6 female mice, ELISPOT analysis showed elevated splenocyte frequencies of IFNγ-producing antigen-specific T cells at a mean of 1 per 3,831 splenocytes, and IL-17 at a mean of 1 per 21,739 splenocytes, but not IL-5 (FIG. 10C).

The proinflammatory T cells responding to AMHR2-ED were predominantly CD4+ T cells but also included CD8$^+$ T cells producing IFNγ (FIG. 10D) and IL-17 (FIG. 10E). Four months after AMHR2-ED vaccination, serum IgG antibody responses against AMHR2-ED were detectable at dilutions up to 1/50,000 (FIG. 10F) and consisted predominantly of IgG1 and IgG2b isotypes (FIG. 10G). AMHR2-ED was highly immunogenic in several mouse strains showing completely divergent major histocompatibility complex haplotypes including C57BL/6 (H-2$^b$), BALB/c (H-2$^d$), A/J (H-2$^a$), and FVBN/J (H-2$^q$) in which IFNγ secreting splenocytes reached frequencies one month after vaccination with means of 1 per 4,310, 1 per 4,425, 1 per 8,772, and 1 per 10,000, respectively (FIG. 10H).

Example 8: Immunogenicity of AMHR2-ED

Figure 11:
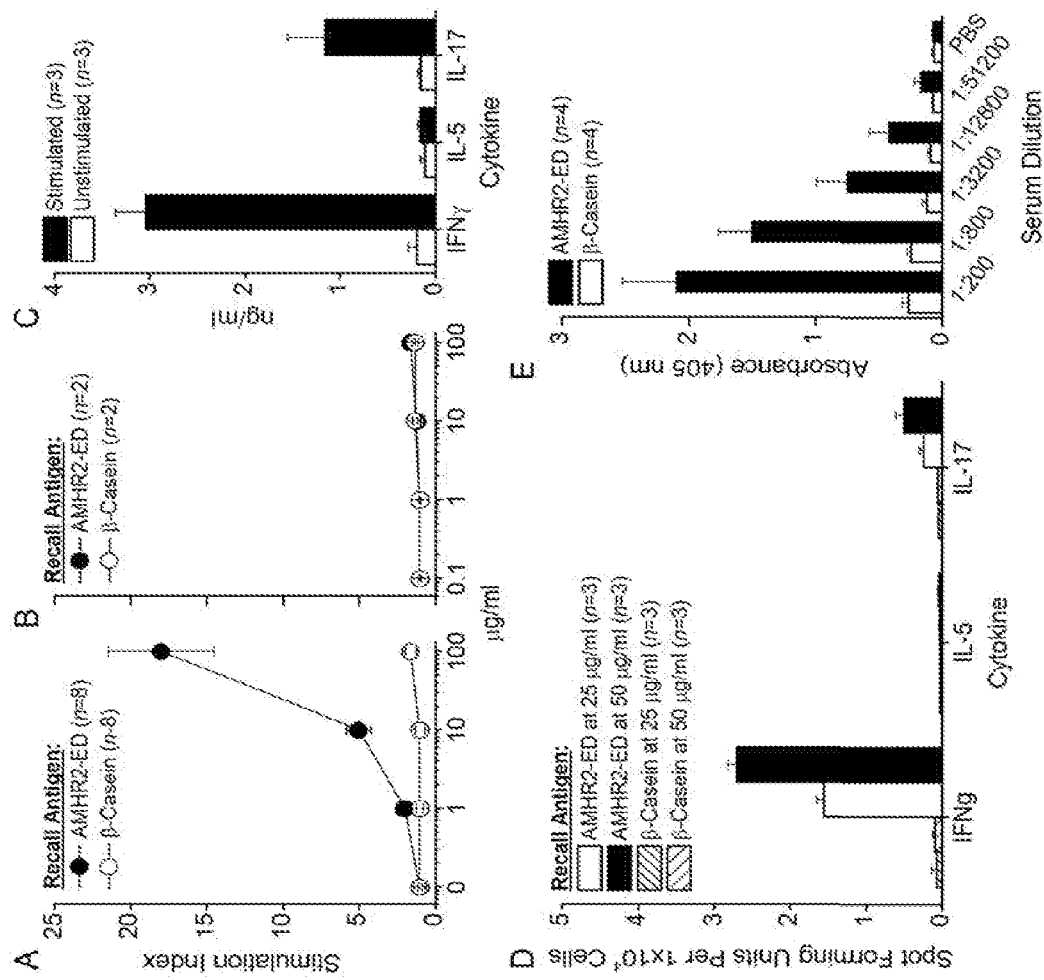
FIG. 11 has five panels and shows that AMHR2-ED is highly immunogenic. Panel (A) shows that splenocytes from AMHR2-ED immunized mice showed antigen-specific recall proliferative responses to AMHR2-ED but not to recombinant mouse β-casein, an irrelevant control antigen generated and purified in a manner similar to AMHR2-ED. Panel (B) shows that splenocytes from CFA immunized mice were unresponsive to both AMHR2-ED and β-casein. Panel (C) depicts an ELISA analysis of culture supernatants, which shows AMHR2-ED activated production of high levels of the proinflammatory cytokines, IFNγ and IL-17, and minimal production of the type-2 regulatory cytokine, IL-5. Panel (D) shows that splenocytes from AMHR2-ED immunized mice demonstrate significantly high frequencies of type-1 (~1/4,000 lymphocytes; $p<0.0001$) and type-17 (~1/20,000 lymphocytes; $p<0.02$) proinflammatory T cells but minimal frequencies of type-2 regulatory T cells expressing IL-5. Panel (E) shows that four months after immunization with AMHR2-EC, serum titers for AMHR2-ED specific IgG were significantly detectable at titers exceeding 1/50,000 dilutions ($p<0.001$).

The immunogenicity of AMHR2-ED was determined by immunization of TgMlSIIR-TAg (DR26 line) transgenic female mice with AMHR2-ED in CFA. Four weeks after immunization, splenocytes from AMHR2-ED showed antigen-specific recall proliferative responses to AMHR2-ED but not to recombinant mouse β-casein, an irrelevant control antigen generated and purified in a manner similar to AMHR2-ED (FIG. 11A). In contrast, splenocytes from CFA-immunized mice were unresponsive to both AMHR2-ED and β-casein (FIG. 11B). ELISA analysis of culture supernatants showed AMHR2-ED activated production of high levels of the proinflammatory cytokines IFNγ and IL-17, and minimal production of the type-2 regulatory cytokine, IL-5 (FIG. 11C). Splenocytes from AMHR2-ED immunized mice showed significantly high frequencies of type-1 (~1/4,000 lymphocytes; p<0.0001) and type-17 (~1/20,000 lymphocytes; p<0.02) proinflammatory T cells but minimal frequencies of type-2 regulatory T cells expressing IL-5 (FIG. 11D). Four months after immunization with AMHR2-ED, serum titers for AMHR2-ED specific IgG were still detectable at titers exceeding 1/50,000 dilutions (p<0.001, FIG. 11E). These results indicate that AMHR2-ED is highly immunogenic.

Figure 12:
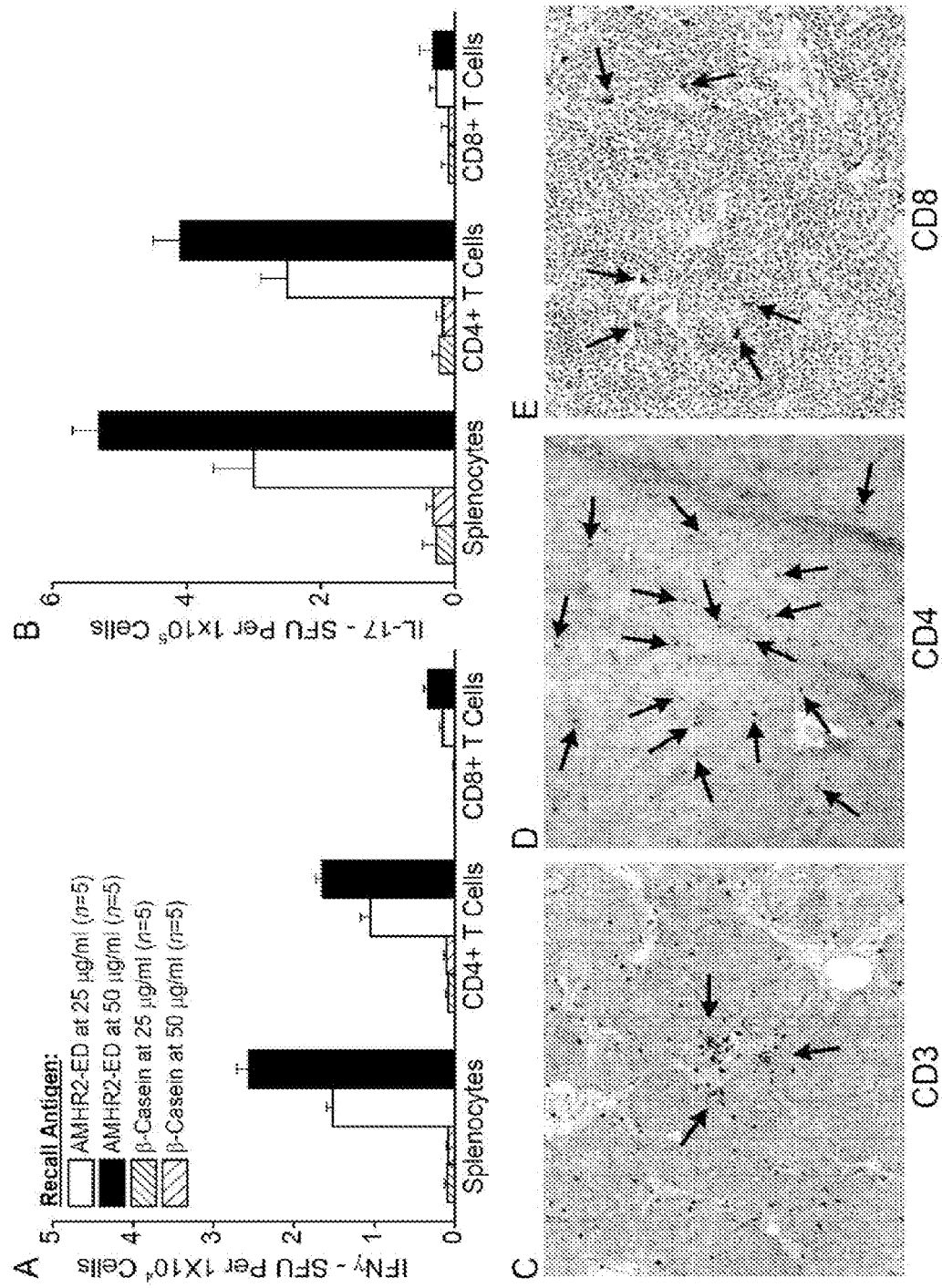
FIG. 12 has five panels and shows that AMHR2-ED activates a predominantly CD4+ T cell response. Splenocytes and purified CD4+ but not CD8+ T cells isolated one month after immunization of TgMISIIR-TAg transgenic female mice with AMHR2-ED showed a prominent antigen-specific induction of type-1 (panel (A)) and type-17 (panel (B)) proinflammatory T cells. Immunohistochemical analysis of autochthonous EOC taken from 7 month old female TgMISIIR-Tag mice that were immunized at 6 weeks of age with AMHR2-ED showed predominant infiltration of CD3+ T cells (panel (C)) and CD4+ T cells (panel (D)), but not CD8+ T cells (panel (E)).

To further evaluate the nature of the immune response generated by vaccination with AMHR2-ED, TgMlSIIR-TAg transgenic female mice were immunized with either AMHR2-ED at 25 μg/ml or 50 μg/ml. One month after immunization, spleens were harvested and IFNγ and IL-17 expression detected. Ass seen in FIG. 12A-B, splenocytes and purified CD4+ but not CD8$^+$ T cells isolated one month after immunization of with AMHR2-ED showed a prominent antigen-specific induction of type-1 and type-17 proinflammatory T cells. Immunohistochemical analysis of autochthonous EOC taken from 7 month old female TgMlSIIR-Tag mice that were immunized at 6 weeks of age with AMHR2-ED showed predominant infiltration of CD3$^+$ T cells and CD4$^+$ T cells, but not CD8$^+$ T cells (FIG. 12C-D).

Example 9. Immunization with AMHR2-ED does not Affect Fertility

Figure 13:
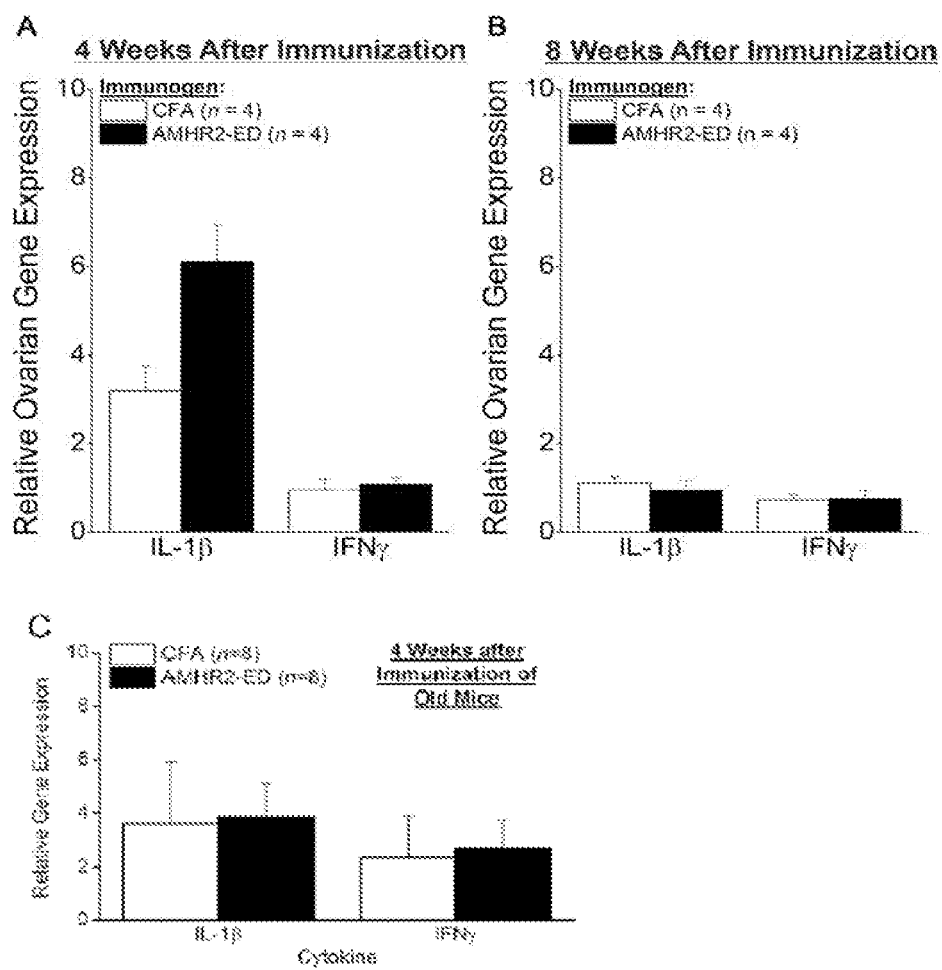
FIG. 13 has three panels and shows transient ovarian inflammation following immunization with AMHR2-ED. Real-time RT-PCR analysis of ovaries taken four weeks (panel (A)) but not 8 weeks (panel (B)) following immunization with AMHR2-ED showed expression of the inflammatory cytokine IL-1β. IFNγ expression was not elevated at time point following immunization. At four weeks (panel (C)) after AMHR2-ED vaccination of 9 month old C57BL/6 female mice, qRT-PCR analysis showed no elevated ovarian gene expression for either IL-1β or IFNγ.

The level of ovarian inflammation following immunization with AMHR2-ED was examined. Ovaries of mice were harvested four weeks and 8 weeks following immunization with AMHR2-ED and analyzed by RT-PCR. As seen in FIG. 13, harvested ovaries showed expression of the inflammatory cytokine IL-1β at four weeks but not at eight weeks following immunization. IFNγ expression was not elevated at either time point following immunization. In contrast, elevated gene expression did not occur for IL-1β or IFNγ in ovaries from 9 month old C57BL/6 female mice at 4 weeks after AMHR2-ED vaccination (FIG. 13C).

Figure 14:
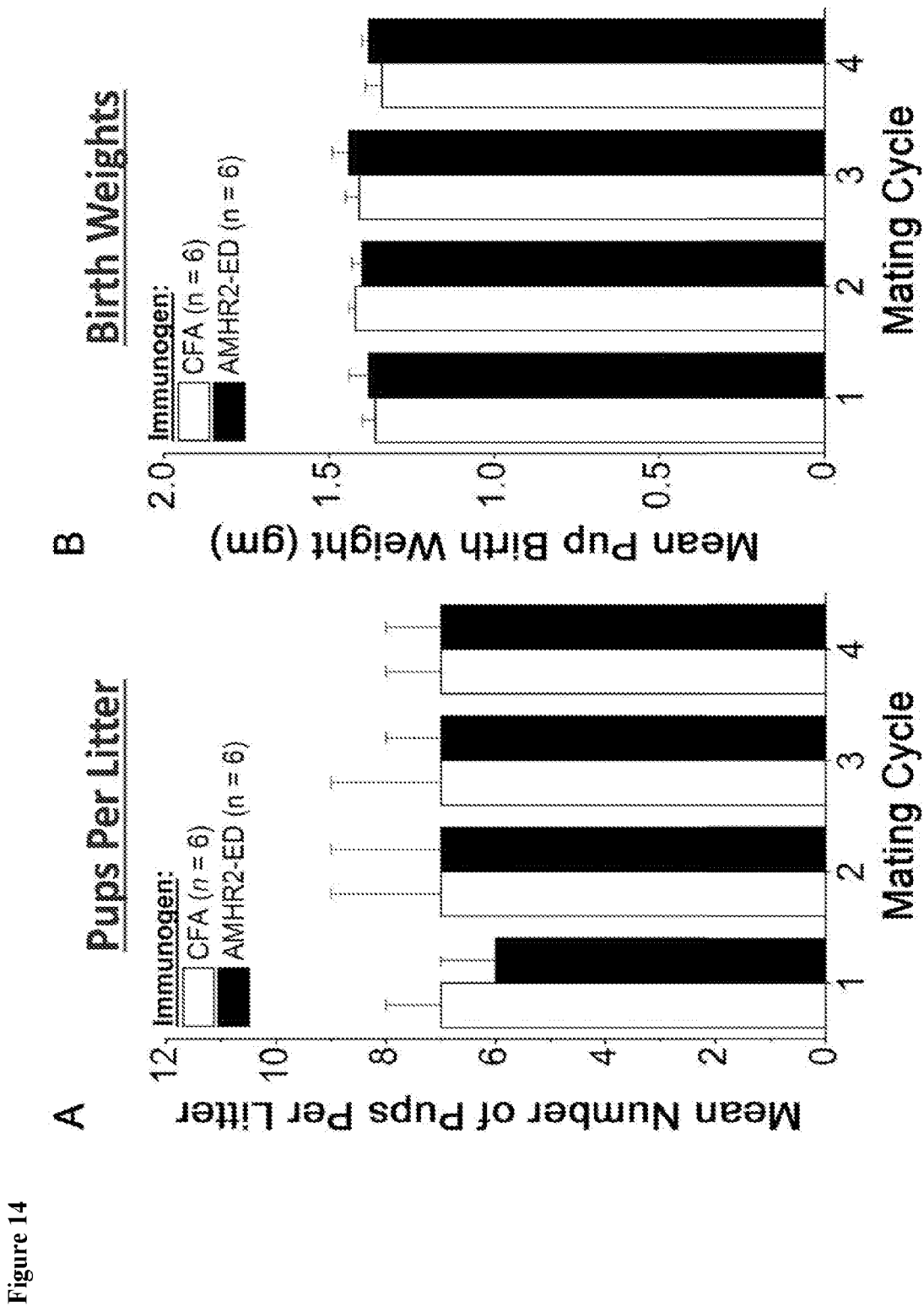
FIG. 14 has two panels and shows that mouse fertility was unaffected by AMHR2-ED immunization. No significant differences in mean number of pups per litter (panel (A)) or mean pup birth weights (panel (B)) were detected between mice immunized with AMHR2-ED in CFA or control mice immunized with CFA alone.

The fertility of mice immunized with AMHR2-ED was next examined. As seen in FIG. 14, ovarian function as measured by fertility over four mating cycles was unaffected by AMHR2-ED immunization. Specifically, no significant differences in mean number of pups per litter or mean pup birth weights were detected between mice immunized with AMHR2-ED in CFA or control mice immunized with CFA alone.

Example 10: Immunization with AMHR2-ED Inhibits Growth of Ovarian Cancer Tumors

Figure 15:
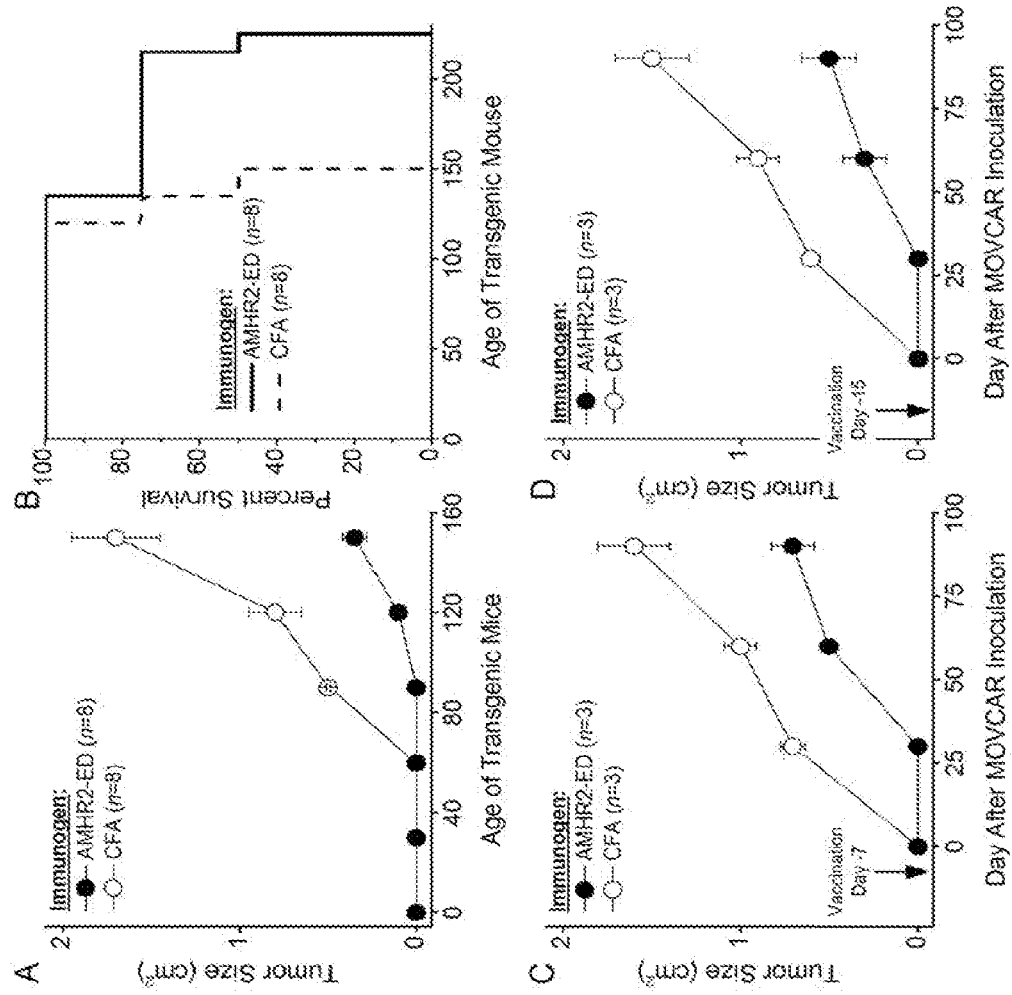
FIG. 15 has eight panels and shows that AMHR2-ED vaccination inhibits growth of authochthonous and transplantable ovarian tumors. Panel (A) shows that prophylactic AMHR2-ED vaccination of female TgMISIIR-TAg transgenic mice at 6-7 weeks of age resulted in a highly significant inhibition in growth of autochthonous EOC ($p<0.0001$). Panel (B) shows that prophylactic AMHR2-ED vaccination of female TgMISIIR-TAg transgenic mice at 6-7 weeks of age resulted in a 42% increased overall survival compared to control mice vaccinated with CFA alone (mean 193.7±34.5 days vs. mean 135±13.89 days). Similar significant inhibition in growth of transplantable TgMISIIR EOC tumors occurred in mice vaccinated either 7 days panel (C) or 15 days panel (D) prior to inoculation with $3×10^6$ mouse ovarian carcinoma (MOVCAR) cells ($p<0.001$). Panel (E) shows prophylactic AMHR2-ED vaccination of 6-7 week old TgMISIIR-TAg (DR26) transgenic mice significantly delayed the appearance and growth of autochthonous EOC tumors. Panel (F) shows the inhibition in growth of autochthonous tumors resulted in a highly significant 42% increased overall survival. Panel (G) shows AMHR2-ED vaccination was also effective in providing significant immunotherapy against EOC in TgMISIIR-TAg (DR26) transgenic mice with established autochthonous tumors. Panel (H) shows immunohistochemical analysis of autochthonous EOC tumors from TgMISIIR-TAg (DR26) mice vaccinated with AMHR2-ED consistently showed prominent infiltrations of CD3+ T cells (upper left panel) and CD4+ T cells (upper middle panel) with occasional CD8+ T cells (upper right panel) indicated by arrows. Corresponding immunostained EOC tumors from control mice vaccinated with CFA alone consistently failed to show detectable T cell infiltrates (lower panels). In all cases, error bars indicate ±SD, and asterisks indicate significance.
Figure 15:
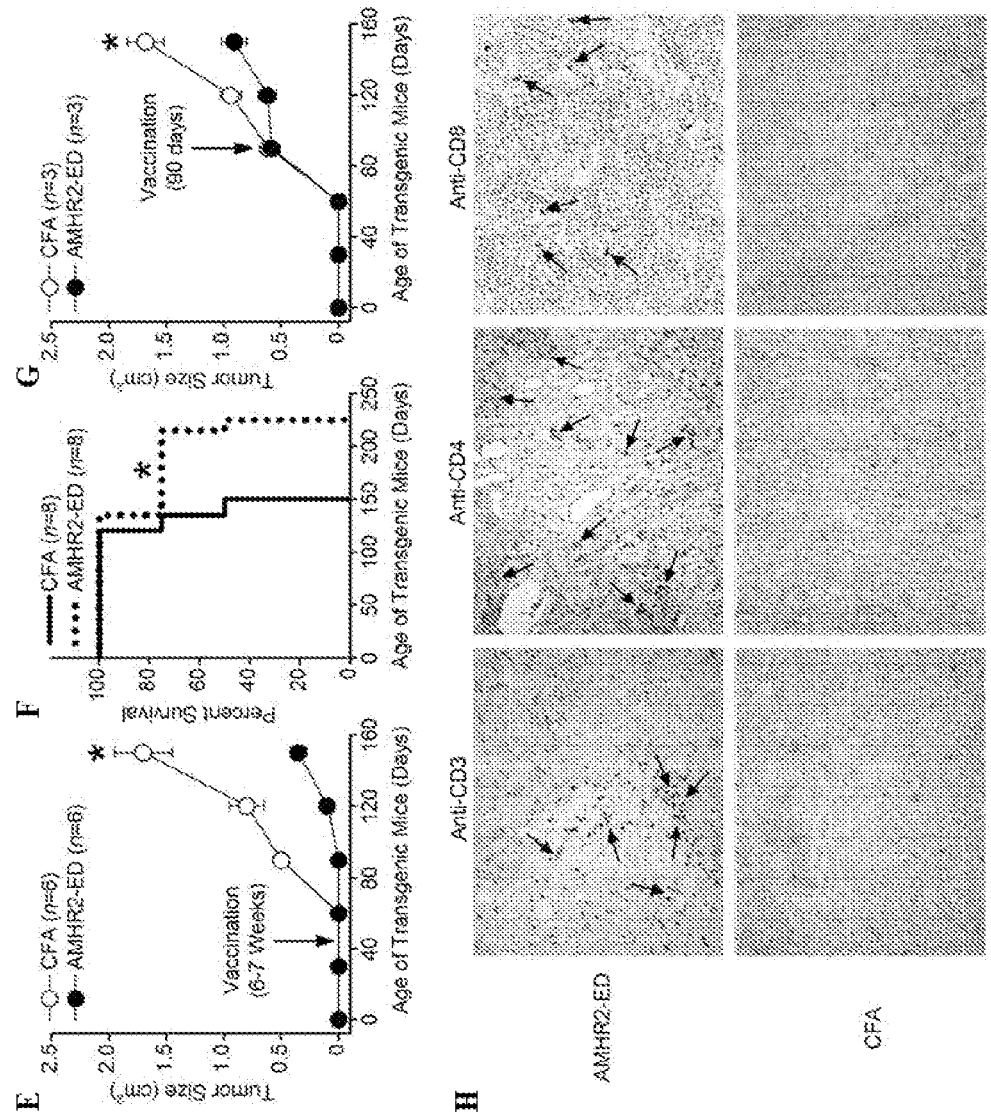

The ability of AMHR2-ED vaccination to inhibit growth of authochthonous and transplantable ovarian tumors was tested. As seen in FIG. 15A-B, prophylactic AMHR2-EC vaccination of female TgMISIIR-TAg transgenic mice at 6-7 weeks of age resulted in a highly significant inhibition in growth of autochthonous EOC ($p<0.0001$) and a 42% increased overall survival compared to control mice vaccinated with CFA alone (mean 193.7±34.5 days vs. mean 135±13.89 days). Similar significant inhibition in growth of transplantable TgMISIIR EOC tumors occurred in mice vaccinated either 7 days or 15 days prior to inoculation with $3 \times 10^6$ mouse ovarian carcinoma (MOVCAR) cells ($p<0.001$; FIG. 15C-D).

Similarly, prophylactic AMHR2-ED vaccination of 6-7 week old TgMISIIR-TAg (DR26) transgenic mice significantly delayed the appearance and growth of autochthonous EOC compared to control mice vaccinated with CFA alone ($P<0.001$; FIG. 15E). This inhibition in the emergence and growth of autochthonous EOC resulted in a highly significant 42% increased overall survival ($P<0.0001$) compared to control mice vaccinated with CFA alone (mean 194±35 days vs. mean 135±14 days, respectively; FIG. 15F). AMHR2-ED vaccination was also effective in providing highly significant immunotherapy against EOC in TgMISIIR-TAg (DR26) transgenic mice with established growing autochthonous EOC ($P<0.0001$; FIG. 15G). Immunohistochemical analysis of autochthonous EOC from TgMISIIR-TAg (DR26) mice vaccinated with AMHR2 consistently showed prominent infiltrates of CD3+ T cells (FIG. 15H, upper left panel) and CD4+ T cells (FIG. 15H, upper middle panel) with occasional CD8+ T cells (FIG. 15H, upper right panel). Corresponding immunostained EOC from control mice vaccinated with CFA alone consistently failed to show detectable T cell infiltrates (FIG. 3f, lower panels).

Figure 16:
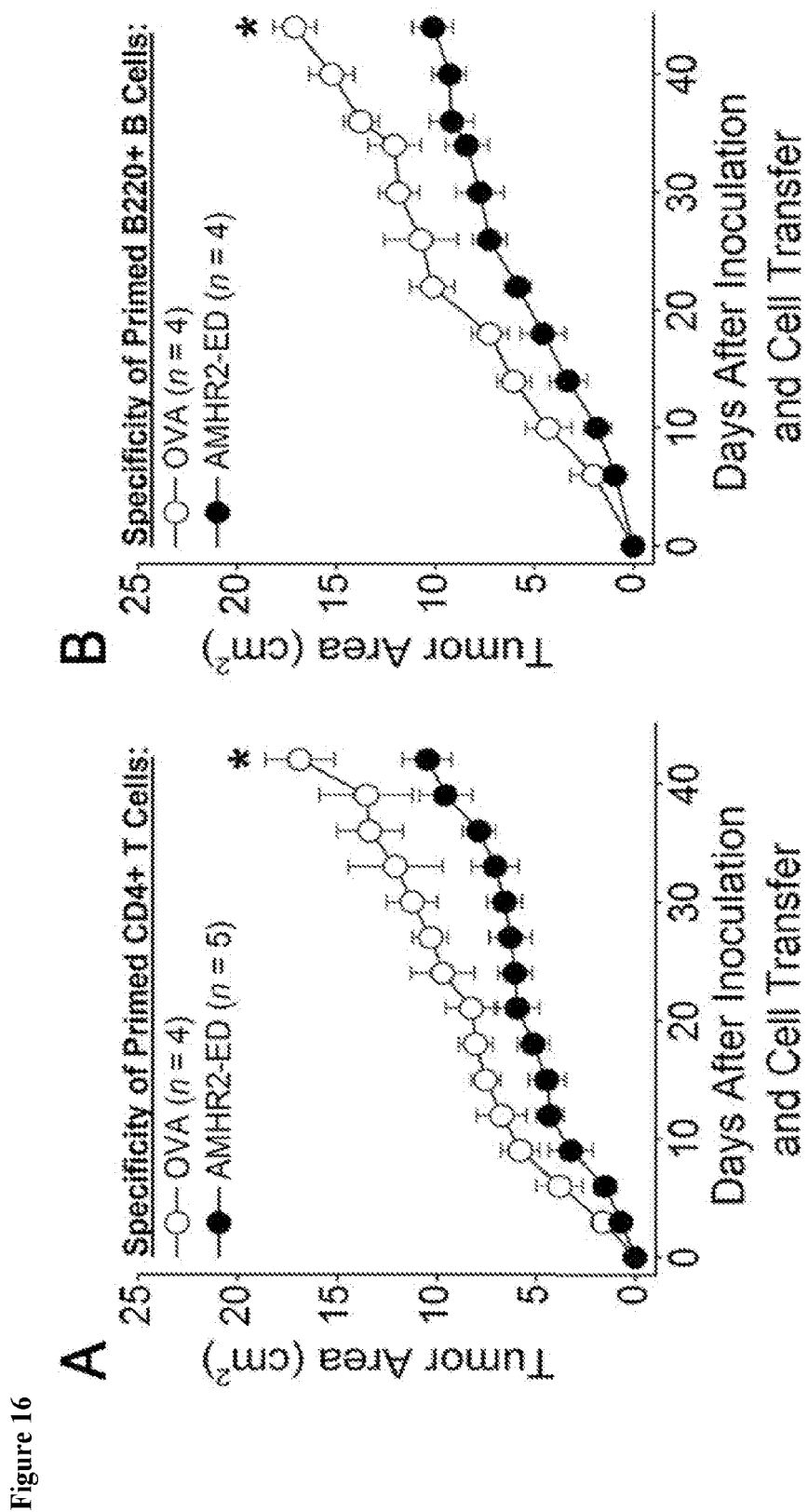
FIG. 16 has two panels and shows inhibition of EOC tumor growth following transfer of AMHR2-ED primed CD4+ T cells and B220+ B cells. Inhibition of growth of MOVCAR EOCs occurred following transfer of CD4+ T cells (panel (A)) or B220+ B cells (panel (B)) from mice immunized with AMHR2-ED. Asterisks indicate significance.
Figure 17:
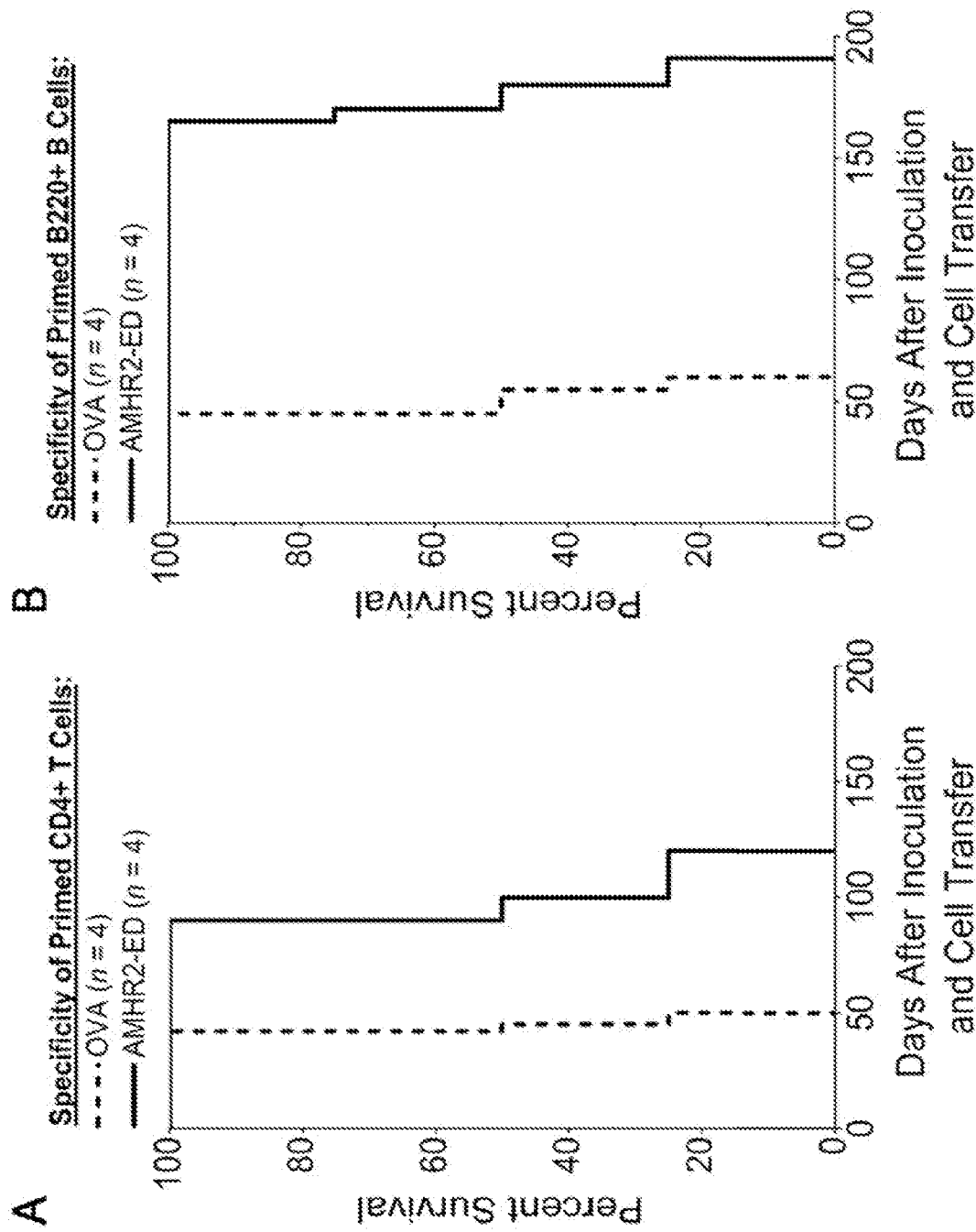
FIG. 17 has two panels and shows increased overall survival following transfer of AMHR2-ED primed CD4+ T cells and B220+ B cells. Increased overall survival in MOVCAR tumor bearing mice that received CD4+ T cells panel (A) or B220+ B cells panel (B) from mice immunized with AMHR2-ED.
Figure 18:
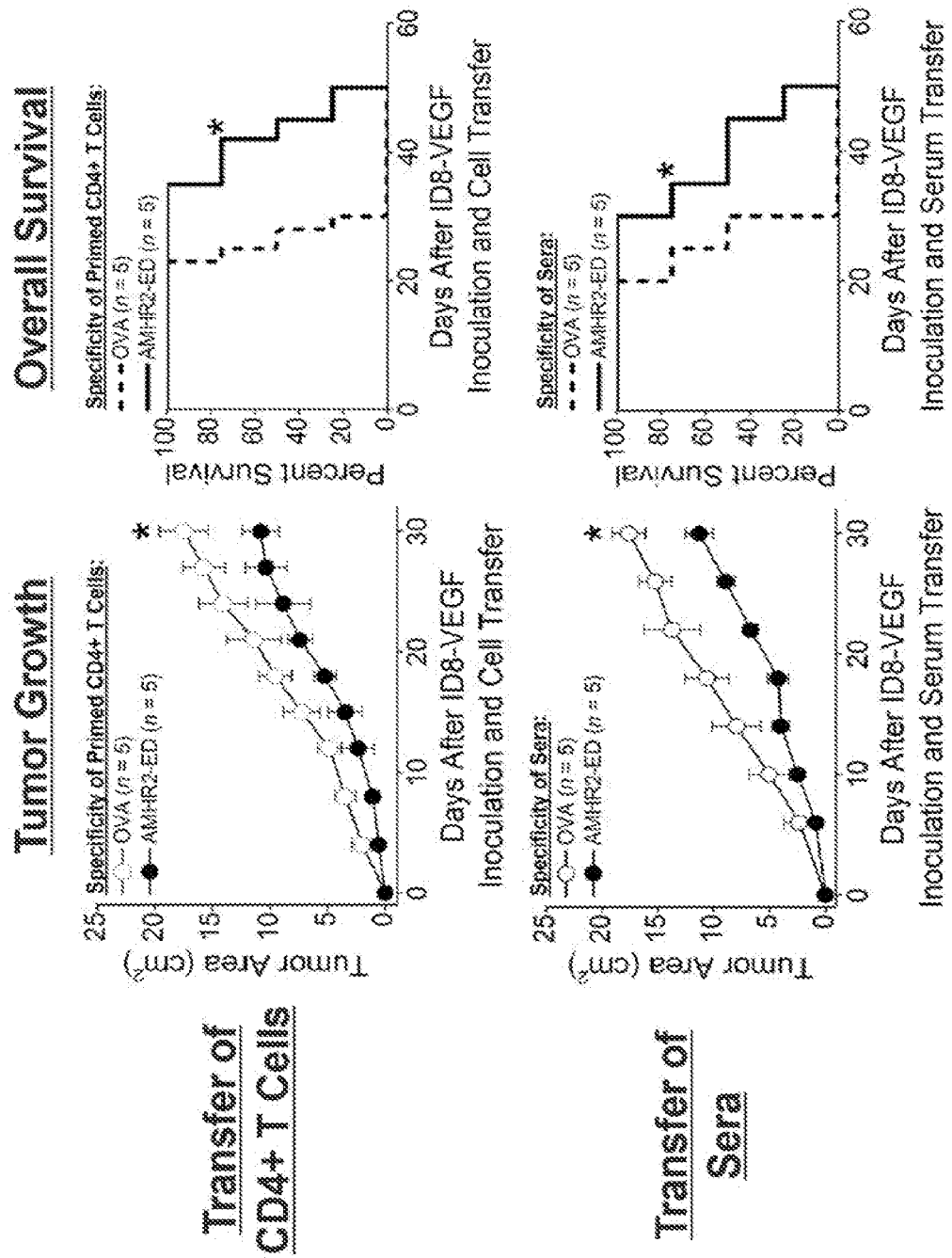
FIG. 18 shows inhibition of tumor growth and enhancement of overall survival following transfer of AMHR2-ED primed CD4+ T cells and sera. Growth inhibition of ID8-VEGF EOC tumors occurred in mice receiving CD4+ T cells (upper left panel) or sera (lower left panel) from mice immunized with AMHR2-ED. Enhanced overall survival occurred in mice that received CD4+ T cells (upper right panel) or sera (lower right panel) from mice immunized with AMHR2-ED.

Example 11. Transfer of AMHR2-ED Primed T Cells and B Cells Inhibits Growth of Ovarian Cancer Tumors The effect of transfer of AMHR2-ED primed CD4+ T cells and B220+ B cells on EOC tumor growth was tested. As seen in FIG. 16, inhibition of growth of MOVCAR EOCs occurred following transfer of CD4+ T cells or B220+ B cells from mice immunized with AMHR2-ED. What is more, as seen in FIG. 17, the transfer of CD4+ T cells or B220+ B cells from AMHR2-ED immunized mice also increased overall survival in MOVCAR tumor bearing mice that received cells. Transfer of cells into naïve recipients and inoculation of MOVCAR EOCs occurred within one day of each other. Additionally, as seen in FIG. 18, growth inhibition of ID8-VEGF EOC tumors occurred in mice receiving CD4+ T cells (upper left panel) or sera (lower left panel) from mice immunized with AMHR2-ED. Enhanced overall survival occurred in mice receiving CD4+ T cells (upper right panel) or sera (lower right panel) from mice immunized with AMHR2-ED. Transfer of cells into naïve recipients and inoculation of ID8-VEGF EOCs occurred within one day of each other. Asterisks indicate significance.

Figure 20:
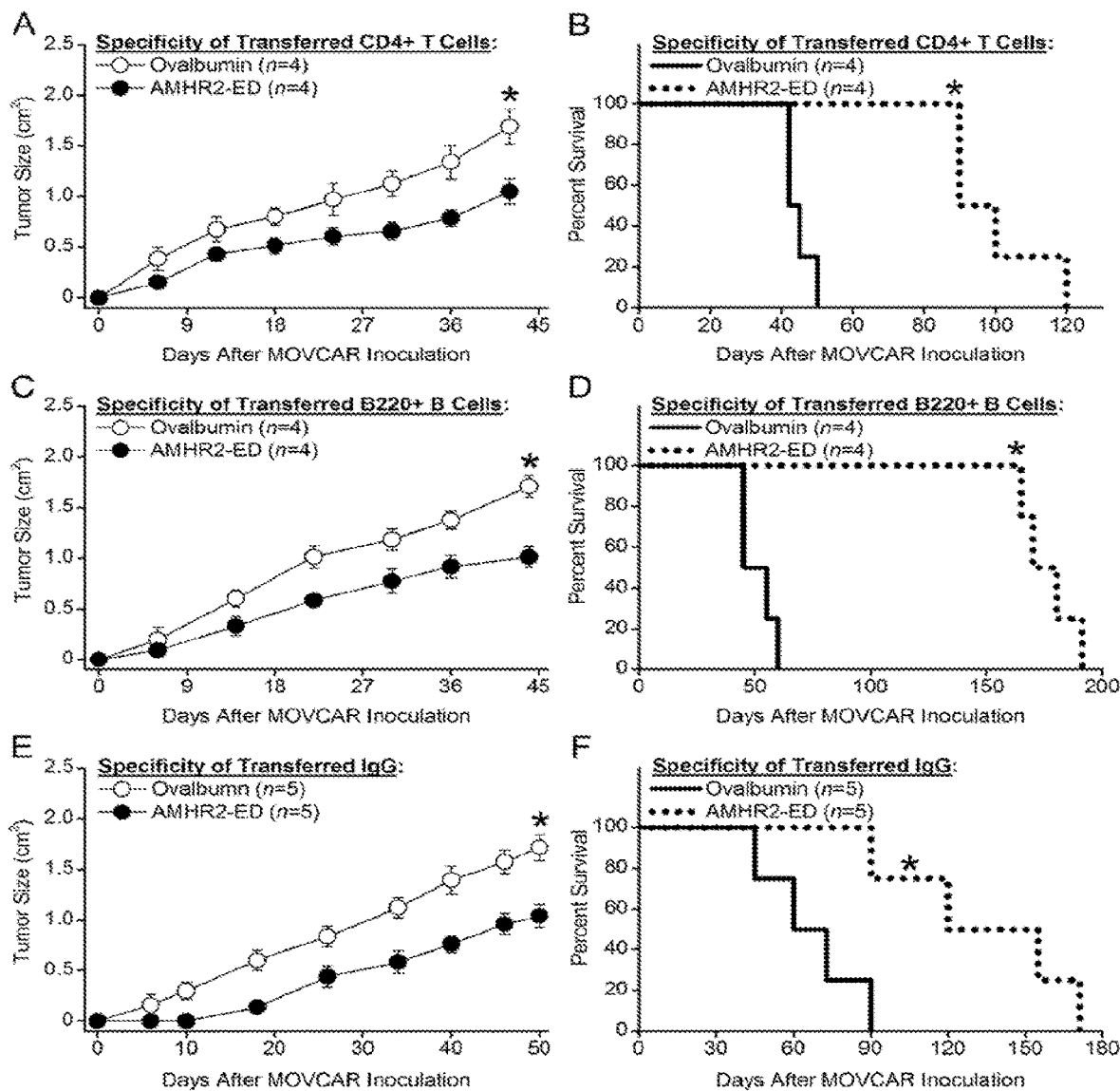
FIG. 20 has six panels and shows the passive transfer of tumor immunity with CD4+ T Cells, B220+ B Cells, and Purified IgG. Panel (A) shows the transfer of AMHR2-ED primed CD4+ T cells into TgMISIIR-TAg (low) female mice one day prior to MOVCAR inoculation resulted in significant inhibition of tumor growth and panel (B) shows enhanced overall survival compared to mice receiving ovalbumin primed CD4+ T cells. Panel (C) shows transfer of AMHR2-ED primed B220+ B cells into TgMISIIR-TAg (low) female mice one day prior to MOVCAR inoculation resulted in significant inhibition of tumor growth and panel (D) shows enhanced overall survival compared to mice receiving B220+ B cells from ovalbumin immunized mice.

Example 12: Passive Transfer of Tumor Immunity with CD4+ T Cells, B220+ B Cells, and IgG The identity of the immune population that accounted for inhibition of EOC tumor growth was tested. It was found that transfer of AMHR2-ED primed CD4+ T cells into TgMISIIR-TAg (low) female mice one day prior to MOVCAR inoculation resulted in highly significant inhibition of tumor growth ($P<0.0001$; FIG. 20A) and enhanced overall survival ($P<0.006$; FIG. 20B) compared to mice receiving ovalbumin primed CD4+ T cells. Moreover, transfer of AMHR2-ED primed B220+ B cells into TgMISIIR-TAg (low) female mice one day prior to MOVCAR inoculation also mediated significant inhibition of tumor growth ($P<0.0001$; FIG. 20C) and enhanced overall survival ($P<0.009$; FIG. 20D) compared to mice receiving B220+ B cells from ovalbumin immunized mice. In addition, transfer of affinity purified IgG from AMHR2-ED immunized mice into TgMISIIR-TAg (low) female mice one day prior to MOVCAR inoculation resulted in significant inhibition of tumor growth ($P<0.0001$; FIG. 20E) and enhanced overall survival ($P<0.002$; FIG. 20F) compared to mice receiving affinity purified IgG from ovalbumin immunized mice.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

SEQUENCE LISTING

```
Sequence total quantity: 32
SEQ ID NO: 1            moltype = AA  length = 573
FEATURE                 Location/Qualifiers
```

```
source                          1..573
                                mol_type = protein
                                organism = Homo sapiens
SEQUENCE: 1
MLGSLGLWAL LPTAVEAPPN RRTCVFFEAP GVRGSTKTLG ELLDTGTELP RAIRCLYSRC  60
CFGIWNLTQD RAQVEMQGCR DSDEPGCESL HCDPSPRAHP SPGSTLFTCS CGTDFCNANY 120
SHLPPPGSPG TPGSQGPQAA PGESIWMALV LLGLFLLLLL LLGSIILALL QRKNYRVRGE 180
PVPEPRPDSG RDWSVELQEL PELCFSQVIR EGGHAVVWAG QLQGKLVAIK AFPPRSVAQF 240
QAERALYELP GLQHDHIVRF ITASRGGPGR LLSGPLLVLE LHPKGSLCHY LTQYTSDWGS 300
SLRMALSLAQ GLAFLHEERW QNGQYKPGIA HRDLSSQNVL IREDGSCAIG DLGLALVLPG 360
LTQPPAWTPT QPQGPAAIME AGTQRYMAPE LLDKTLDLQD WGMALRRADI YSLALLLWEI 420
LSRCPDLRPD SSPPPFQLAY EAELGNTPTS DELWALAVQE RRRPYIPSTW RCFATDPDGL 480
RELLEDCWDA DPEARLTAEC VQQRLAALAH PQESHPFPES CPRGCPPLCP EDCTSIPAPT 540
ILPCRPQRSA CHFSVQQGPC SRNPQPACTL SPV                             573

SEQ ID NO: 2                    moltype = DNA   length = 25
FEATURE                         Location/Qualifiers
source                          1..25
                                mol_type = other DNA
                                organism = synthetic construct
SEQUENCE: 2
ccccggggta gcctgcggtt cctgc                                       25

SEQ ID NO: 3                    moltype = DNA   length = 22
FEATURE                         Location/Qualifiers
source                          1..22
                                mol_type = other DNA
                                organism = synthetic construct
SEQUENCE: 3
ctgagccgct gttccgattt ga                                          22

SEQ ID NO: 4                    moltype = DNA   length = 22
FEATURE                         Location/Qualifiers
source                          1..22
                                mol_type = other DNA
                                organism = synthetic construct
SEQUENCE: 4
atgttggggc gcttcctctc ct                                          22

SEQ ID NO: 5                    moltype = DNA   length = 20
FEATURE                         Location/Qualifiers
source                          1..20
                                mol_type = other DNA
                                organism = synthetic construct
SEQUENCE: 5
cgggcagctg caaggaaaac                                             20

SEQ ID NO: 6                    moltype = DNA   length = 20
FEATURE                         Location/Qualifiers
source                          1..20
                                mol_type = other DNA
                                organism = synthetic construct
SEQUENCE: 6
ccccggctgg cagtgataaa                                             20

SEQ ID NO: 7                    moltype = DNA   length = 21
FEATURE                         Location/Qualifiers
source                          1..21
                                mol_type = other DNA
                                organism = synthetic construct
SEQUENCE: 7
gcggggaagc acaaagacac t                                           21

SEQ ID NO: 8                    moltype = DNA   length = 20
FEATURE                         Location/Qualifiers
source                          1..20
                                mol_type = other DNA
                                organism = synthetic construct
SEQUENCE: 8
ccggccatgg gtaagattcc                                             20

SEQ ID NO: 9                    moltype = DNA   length = 21
FEATURE                         Location/Qualifiers
source                          1..21
                                mol_type = other DNA
                                organism = synthetic construct
SEQUENCE: 9
ggggctttgg gcattacttc c                                           21
```

-continued

```
SEQ ID NO: 10            moltype = DNA   length = 20
FEATURE                  Location/Qualifiers
source                   1..20
                         mol_type = other DNA
                         organism = synthetic construct
SEQUENCE: 10
ccggtcttgg gtcaggttcc                                                       20

SEQ ID NO: 11            moltype = DNA   length = 28
FEATURE                  Location/Qualifiers
source                   1..28
                         mol_type = other DNA
                         organism = synthetic construct
SEQUENCE: 11
ggatccaagg cctgcagagt gcaaggtg                                              28

SEQ ID NO: 12            moltype = DNA   length = 27
FEATURE                  Location/Qualifiers
source                   1..27
                         mol_type = other DNA
                         organism = synthetic construct
SEQUENCE: 12
aagcttctac tcatttacat acacctg                                               27

SEQ ID NO: 13            moltype = DNA   length = 20
FEATURE                  Location/Qualifiers
source                   1..20
                         mol_type = other DNA
                         organism = synthetic construct
SEQUENCE: 13
tgcatggtgt acaacattcc                                                       20

SEQ ID NO: 14            moltype = DNA   length = 21
FEATURE                  Location/Qualifiers
source                   1..21
                         mol_type = other DNA
                         organism = synthetic construct
SEQUENCE: 14
ttgggactgt gaatcaatgc c                                                     21

SEQ ID NO: 15            moltype = DNA   length = 22
FEATURE                  Location/Qualifiers
source                   1..22
                         mol_type = other DNA
                         organism = synthetic construct
SEQUENCE: 15
ggatatctgg aggaactggc aa                                                    22

SEQ ID NO: 16            moltype = DNA   length = 22
FEATURE                  Location/Qualifiers
source                   1..22
                         mol_type = other DNA
                         organism = synthetic construct
SEQUENCE: 16
tgatggcctg attgtctttc aa                                                    22

SEQ ID NO: 17            moltype = DNA   length = 20
FEATURE                  Location/Qualifiers
source                   1..20
                         mol_type = other DNA
                         organism = synthetic construct
SEQUENCE: 17
cgagtgacaa gcctgtagcc                                                       20

SEQ ID NO: 18            moltype = DNA   length = 20
FEATURE                  Location/Qualifiers
source                   1..20
                         mol_type = other DNA
                         organism = synthetic construct
SEQUENCE: 18
gtgggtgagg agcacgtagt                                                       20

SEQ ID NO: 19            moltype = DNA   length = 24
FEATURE                  Location/Qualifiers
source                   1..24
                         mol_type = other DNA
                         organism = synthetic construct
SEQUENCE: 19
aaggagaacc aagcaacgac aaaa                                                  24
```

```
SEQ ID NO: 20          moltype = DNA   length = 24
FEATURE                Location/Qualifiers
source                 1..24
                       mol_type = other DNA
                       organism = synthetic construct
SEQUENCE: 20
tggggaactc tgcagactca aact                                              24

SEQ ID NO: 21          moltype = DNA   length = 20
FEATURE                Location/Qualifiers
source                 1..20
                       mol_type = other DNA
                       organism = synthetic construct
SEQUENCE: 21
gcaggccaca gaattgaaag                                                   20

SEQ ID NO: 22          moltype = DNA   length = 20
FEATURE                Location/Qualifiers
source                 1..20
                       mol_type = other DNA
                       organism = synthetic construct
SEQUENCE: 22
tccaccacag ttgctgactc                                                   20

SEQ ID NO: 23          moltype = DNA   length = 20
FEATURE                Location/Qualifiers
source                 1..20
                       mol_type = other DNA
                       organism = synthetic construct
SEQUENCE: 23
acacacctgt gcaagaagca                                                   20

SEQ ID NO: 24          moltype = DNA   length = 20
FEATURE                Location/Qualifiers
source                 1..20
                       mol_type = other DNA
                       organism = synthetic construct
SEQUENCE: 24
gctcttgttg gttgggaatc                                                   20

SEQ ID NO: 25          moltype = DNA   length = 19
FEATURE                Location/Qualifiers
source                 1..19
                       mol_type = other DNA
                       organism = synthetic construct
SEQUENCE: 25
ttacatctgg gcacccttg                                                    19

SEQ ID NO: 26          moltype = DNA   length = 21
FEATURE                Location/Qualifiers
source                 1..21
                       mol_type = other DNA
                       organism = synthetic construct
SEQUENCE: 26
ttgccttcct gtctgactag c                                                 21

SEQ ID NO: 27          moltype = DNA   length = 20
FEATURE                Location/Qualifiers
source                 1..20
                       mol_type = other DNA
                       organism = synthetic construct
SEQUENCE: 27
ggtcatcact attggcaacg                                                   20

SEQ ID NO: 28          moltype = DNA   length = 20
FEATURE                Location/Qualifiers
source                 1..20
                       mol_type = other DNA
                       organism = synthetic construct
SEQUENCE: 28
acggatgtca acgtcacact                                                   20

SEQ ID NO: 29          moltype = DNA   length = 20
FEATURE                Location/Qualifiers
source                 1..20
                       mol_type = other DNA
                       organism = synthetic construct
SEQUENCE: 29
```

```
gtatccgctg cctctacagc                                                    20

SEQ ID NO: 30          moltype = DNA  length = 20
FEATURE                Location/Qualifiers
source                 1..20
                       mol_type = other DNA
                       organism = synthetic construct
SEQUENCE: 30
cagaagtcag tgccacagga                                                    20

SEQ ID NO: 31          moltype = DNA  length = 25
FEATURE                Location/Qualifiers
source                 1..25
                       mol_type = other DNA
                       organism = synthetic construct
SEQUENCE: 31
agcccgaacc gccgccgcac ctgtg                                              25

SEQ ID NO: 32          moltype = AA  length = 6
FEATURE                Location/Qualifiers
source                 1..6
                       mol_type = protein
                       organism = synthetic construct
SEQUENCE: 32
HHHHHH                                                                    6
```

We claim:

1. A method of eliciting an AMHR2-specific immune response in a female human subject comprising: administering to the subject an immunogenic composition comprising a nucleic acid encoding an Anti-Mullerian Hormone Receptor, Type II (AMHR2) polypeptide,
    wherein the AMHR2 polypeptide comprises the extracellular domain of human AMHR2, wherein the immunogenic composition elicits an immune response specific for an AMHR2 polypeptide comprising the extracellular domain of human AMHR2.

2. The method of claim 1, wherein the nucleic acid encoding the AMHR2 polypeptide is an expression vector encoding the AMHR2 polypeptide.

3. The method of claim 1, wherein the nucleic acid encoding the AMHR2 polypeptide comprises an mRNA encoding the AMHR2 polypeptide.

4. The method of claim 1, wherein the nucleic acid encoding the AMHR2 polypeptide is operably incorporated into a delivery vector.

5. The method of claim 4 wherein the delivery vector is selected from biodegradable microcapsules, immune-stimulating complexes, and liposomes.

6. The method of claim 5, wherein the delivery vector is a viral vector.

7. The method of claim 6, wherein the viral vector is an adenovirus, an adeno-associated virus, a vaccinia virus, or a baculovirus.

8. The method of claim 1, wherein the immunogenic composition comprises an adjuvant.

9. The method of claim 8, wherein the adjuvant is selected from:
    Adjuvant 65, α-GalCer, aluminum phosphate, aluminum hydroxide, calcium phosphate, β-Glucan Peptide, CpG DNA, GM-CSF, GPI-0100, IFA, IFN-γ, IL-17, lipid A, lipopolysaccharide, Lipovant, Montanide, N-acety 1-muramy 1-L-alany 1-D-isoglutamine, Pam3CSK4, poly-IC, quil A, trehalose dimycolate and zymosan.

10. The method of claim 8, wherein the adjuvant comprises aluminum.

11. The method of claim 8, wherein the adjuvant is one that induces a mixed type I/type 17 immune response.

12. The method of claim 1, further comprising a step of determining whether the subject comprises an ovarian cancer tumor that expresses AMHR2.

13. The method of claim 1, wherein the female human subject comprises a BRCA1 or BRCA2 mutation in their genome.

14. The method of claim 1, wherein the female human subject has a family history of ovarian cancer.

15. A method comprising vaccinating a female human subject with a vaccine comprising an immunogenic composition comprising a human Anti-Mullerian Hormone Receptor, Type II (AMHR2) extracellular domain polypeptide or a human AMHR2 cytoplasmic domain polypeptide.

16. A method comprising vaccinating a female human subject with a vaccine comprising an immunogenic composition comprising a nucleic acid encoding a human Anti-Mullerian Hormone Receptor, Type II (AMHR2) extracellular domain polypeptide or a nucleic acid encoding a human AMHR2 cytoplasmic domain polypeptide.

17. The method of claim 15, wherein the immunogenic composition comprises a human Anti-Mullerian Hormone Receptor, Type II (AMHR2) extracellular domain polypeptide.

18. The method of claim 16, wherein the immunogenic composition comprises a nucleic acid encoding a human Anti-Mullerian Hormone Receptor, Type II (AMHR2) extracellular domain polypeptide.

* * * * *